United States Patent [19]

Ishizumi et al.

[11] Patent Number: 4,673,668
[45] Date of Patent: Jun. 16, 1987

[54] AMINONAPHTHACENE DERIVATIVES

[75] Inventors: Kikuo Ishizumi, Toyonaka; Naohito Ohashi, Nishinomiya; Norihiko Tanno, Ibaraki; Hiromi Sato; Masaru Fukui, both of Toyonaka; Shinya Morisada, Takarazuka, all of Japan

[73] Assignee: Sumitomo Pharmaceuticals Company, Osaka, Japan

[21] Appl. No.: 721,606

[22] Filed: Apr. 10, 1985

Related U.S. Application Data

[63] Continuation-in-part of Ser. No. 543,967, Oct. 20, 1983, abandoned.

[30] Foreign Application Priority Data

Oct. 22, 1982 [JP] Japan .................. 57-186514

[51] Int. Cl.$^4$ ...................... A61K 31/71; C07H 15/24
[52] U.S. Cl. ............................... 514/34; 536/6.4
[58] Field of Search ............................ 536/6.4; 514/34

[56] References Cited

U.S. PATENT DOCUMENTS

| | | | |
|---|---|---|---|
| 4,075,328 | 2/1978 | Ducep et al. | 536/6.4 |
| 4,218,440 | 8/1980 | Penco et al. | 536/6.4 |
| 4,540,695 | 9/1985 | Ishizumi et al. | 260/365 |

FOREIGN PATENT DOCUMENTS

| 72259 | 2/1983 | European Pat. Off. | 260/365 |
|---|---|---|---|

OTHER PUBLICATIONS

Iwamoto, *Tetrahedron Letters*, No. 36, pp. 3891-3894, 1968.
Johnson et al. *Cancer Trestment Reviews*, 2 pp. 1-31, 1975.
Horton, *Carbohydrate Research*, vol. 76 (1979), pp. 269-276.

*Primary Examiner*—Johnnie R. Brown
*Assistant Examiner*—Elli Peselev
*Attorney, Agent, or Firm*—Cushman, Darby & Cushman

[57] ABSTRACT

9-Aminonaphthacene derivative having the formula:

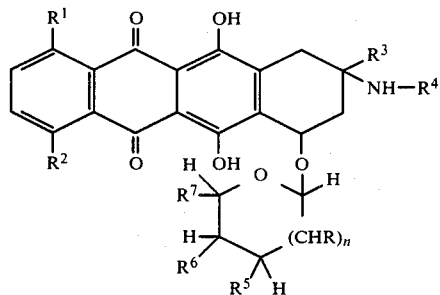

wherein $R^1$ and $R^2$ are both hydrogen atoms or either one of them is a hydrogen atom and the other is hydroxy group or methoxy group; $R^3$ is acetyl group or 1-hydroxyethyl group; $R^4$ is a hydrogen atom; $R^5$ is a hydrogen atom, hydroxy group, lower alkanoyloxy group, amino group, halogen-substituted lower alkanoylamino group or morpholino group; $R^6$ is a hydrogen atom, hydroxy group, lower alkanoyloxy group or tetrahydropyranyloxy group; $R^7$ is a hydrogen atom or methyl group; R is a hydrogen atom; and n is zero or one, which is useful as anti-cancer chemical agents with lower toxicity and with little local irritation and is able to orally be applied.

19 Claims, No Drawings

AMINONAPHTHACENE DERIVATIVES

This is a continuation-in-part application of Ser. No. 543,967 filed on Oct. 20, 1983 now abandoned.

The present invention relates to novel aminonaphthacene derivatives and processes preparing the same. More particularly, the present invention concerns aminonaphthacene derivatives having the formula (I):

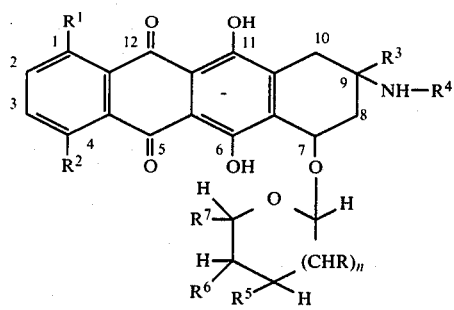

wherein $R^1$ and $R^2$ are both hydrogen atoms or either one of them is a hydrogen atom and the other is hydroxy group or methoxy group; $R^3$ is acetyl group or 1-hydroxy ethyl group; $R^4$ is a hydrogen atom; $R^5$ is a hydrogen atom, hydroxy group, lower alkanolyoxy group, amino group, halogen-substituted lower alkanoyl amino group, morpholino group; $R^6$ is a hydrogen atom, hydroxy group, lower alkanoyloxy group, tetrahydropyranyloxy group; $R^7$ is a hydrogen atom or methyl group; R is a hydrogen atom; and n is zero or one.

In the foregoing and subsequent descriptions, the term "lower alkanoyl" is intended to mean any group having $C_{1-4}$ alkanoyl group. The term "halogen-substituted lower alkanoyl group" is intended to mean any group of $C_{1-4}$ alkanoyl group substituted with one to three fluorine atoms, chlorine atoms, bromine atoms or iodine atoms.

Aminonaphthacene derivative having the formula (I) is analogous to anthracycline antibiotics which are familiar therapeutic chemicals for cancer clinically administered. Although "Dounomycin" and "Adoriamycin" are known as anthracycline antibiotics having strong anti-tumor activity and are clinically useful [Process Biochemistry 12-16 (1980)], they are not satisfactory yet.

The present invention provides compounds (I) which are useful as an anti-cancer chemical agents with lower toxicity and with little local irritation and are able to orally be applied.

The aminonaphthacene derivatives (I) can be administered parenterally, orally or locally to warmblooded animals and human beings in the form of conventional pharmaceutical preparations. For instance, they can be administered in the form of conventional solid pharmaceutical preparations such as tablets, capsules, powders or granules, or in the form of conventional liquid pharmaceutical preparations such as suspensions, emulsions or solutions. The daily dosage may vary depending upon the administration route and is usually between 0.1 to 100 mg/kg.

Aminonaphthacene derivative having the formula (IV) which is one of aminonaphthacene derivatives having the formula (I):

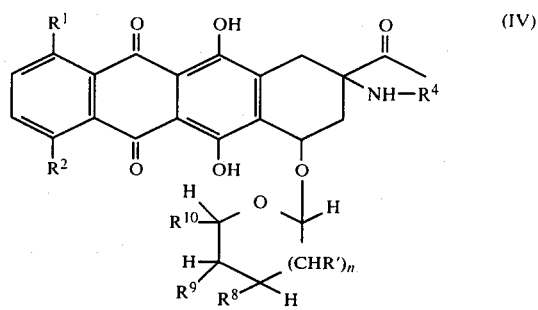

wherein
$R^1$, $R^2$, $R^4$ and n are as defined above;
$R^8$ is a hydrogen atom, lower alkanoyloxy group, halogen-substituted lower alkanoyloxy group, or halogen-substituted lower alkanoyl amino group;
R' and $R^9$ are a hydrogen atom, lower alkanoyloxy group, or halogen-substituted lower alkanoyloxy group, respectively; and
$R^{10}$ is a hydrogen atom, methyl group, lower alkanoyloxymethyl group or halogen-substituted lower alkanoyloxymethyl group; is prepared according to the following process (A) or (B).

(A) Glucosylating a compound having the formula (II):

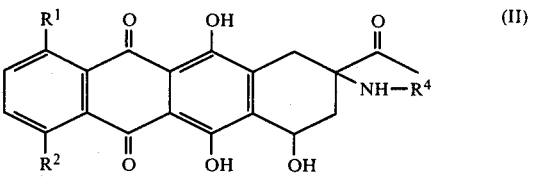

wherein $R^1$, $R^2$ and $R^4$ are as defined above: with a saccharide derivative having the formula (III):

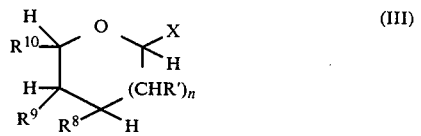

wherein R', $R^8$, $R^9$, $R^{10}$ and n are as defined above; and X is a chlorine atom or a bromine atom; in the presence of either a soluble silver salt such as silver salt of trifluoromethane sulfonic acid, etc., or a mercuric salt such as mercuric oxide, mercuric cyanate, and mercuric bromide, etc., in a solvent of a halogenated alkyl solvent such as dichloromethane and dichloroethane, etc., an ethereal solvent such as tetrahydrofuran and diethylether, etc., or a mixture thereof;

(B) Glucosylating a compound having the formula (II) with one of compounds having the formulas (V) and (VI):

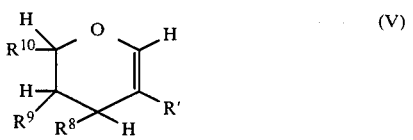

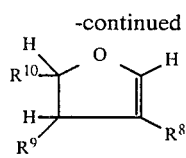

(VI)

wherein R', R⁸, R⁹ and R¹⁰ are as defined above; in the presence of an acidic catalyst such as methane sulfonic acid, p-toluene sulfonic acid, in an anhydrous organic solvent such as dimethylformamide, benzene, toluene, tetrahydrofuran and dioxane, etc.

Compound having the formula (IV) obtained according to the glycosylating reaction above is usually a mixture of two forms of compounds with respect to configuration of sugar component, i.e., (1) 1'α-combination (α-anomer) and (2) 1'α-combination (β-anomer).

Stereoisomers of compound having the formula (IV) are discussed below. There are two forms of compounds in the starting compound having the formula (II) in respect to configuration of the oxygen atom at 7-position and the nitrogen atom at 9-position, i.e., cis form and trans form. For instance, compound having the formula (IV) is given in the form of a mixture of four steric isomers when the glycosylating reaction is carried out between racemate of the compound (II) in cis form and optically active compound selected from sugar derivatives having the formulas (III), (V) and (VI). Also, a mixture of two steric isomers is obtained when the glycosylating reaction is effected between optically active form of the compound (II), e.g., cis form, and the optically active sugar derivative. Isomers above can be separated from each other by means of chromatography using, for example, silica gel. Alternatively, the separation may be effected after hydrolysis discussed hereinafter.

Hydrolysis of ester group of aminonaphthacene derivatives having the formula (IV) and having ester group to obtain aminonaphthacene derivative having the formula (VII):

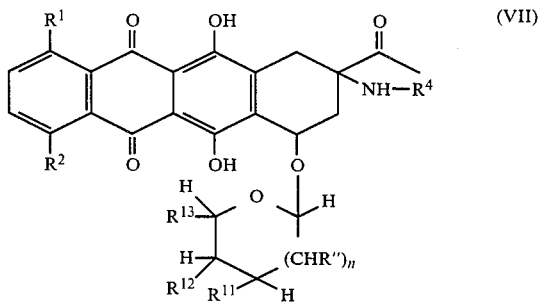

(VII)

wherein R¹, R², R⁴ and n are defined above; R¹¹ is a hydrogen atom, hydroxy group or halogen-substituted lower alkanoylamino group; R" and R¹² are a hydrogen atom or hydroxy group, respectively; R¹³ is a hydrogen atom, methyl group or hydroxymethyl group but R¹³ is not a hydrogen atom nor methyl group when both R¹¹ and R¹² are hydrogen atoms, may be carried out with inorganic bases such as sodium hydroxide, potassium carbonate, sodium hydrogen carbonate etc. or with organic bases such as triethylamine, in a solvent such as methanol, ethanol, hydrous tetrahydrofuran, hydrous acetone etc. Hydrolysis above of the compound where ester group is trifluoroacetoxy group may be effected under milder conditions than those to be applied for the other ester groups, for example, with triethylamine or sodium hydrogen carbonate in methanol or hydrous acetone. Hydrolysis of aminonaphthacene derivative having the formula (IV) above and containing trifluoroacetamido group in addition to ester group may be effected under such conditions that the trifluoroacetamido group is hardly hydrolysed, for example, with potassium carbonate, at a temperature of from −20° C. to 5° C. for a period of time from 0.5 to 2 hours, resulting in aminonaphthacene derivative having the formula (VII) and having trifluoroacetamido group as well as hydroxy group.

A compound having the formula (VIII):

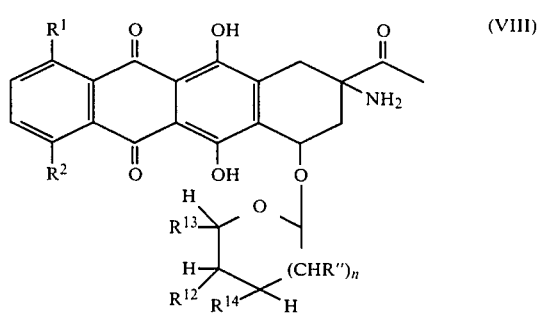

(VIII)

wherein R", R¹, R², R¹², R¹³ and n are defined above and R¹⁴ is a hydrogen atom, hydroxy group, amino group or halogen-substituted lower alkanoylamino group excluding trifluoroacetamido group, is prepared from an aminonaphthacene derivative having the formula (IV) and R⁴ is trifluoroacetyl group. When there is ester group in the molecule of the compound having the formula (IV), there are two procedures. One is that the ester group is first hydrolysed according to the above procedure before the trifluoroacetamido group is hydrolysed; and another is that both the ester group and the trifluoroacetamido group are hydrolysed at one time. In the former procedure a compound having the trifluoroacetamide group obtained from hydrolysis of the ester group is allowed to react with an inorganic base such as sodium hydroxide, potassium carbonate, etc., in a solvent such as methanol, hydrous acetone, hydrous tetrahydrofuran, etc., at a temperature of from 0° C. to 10° C. for from 0.5 to 20 hours, resulting in hydrolysis of the trifluoroacetamido group until a compound having the formula (VIII) is obtained. In the latter procedure, the hydrolysis is effected under the conditions above where the trifluoroacetamide group as well as the ester group are hydrolysed, until a compound having the formula (VIII) is obtained. A compound having the formula (VIII) is also obtained by hydrolysis of a compound having the formula (IV) where R⁴ is trifluoroacetyl group and there is no ester group in the molecule, under the same conditions as in the latter procedure above.

A compound having the formula (X):

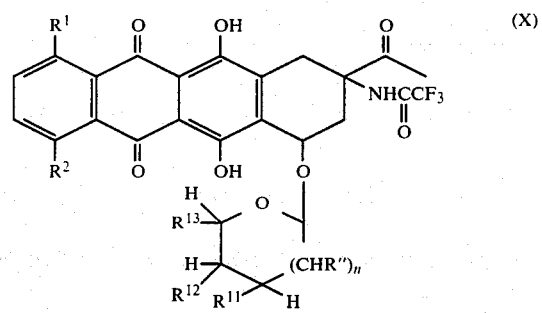

(X)

wherein R'', $R^1$, $R^2$, $R^{11}$, $R^{12}$, $R^{13}$ and n are as defined above, is obtained by allowing a compound having the formula (IX), one of compounds having the formula (IV):

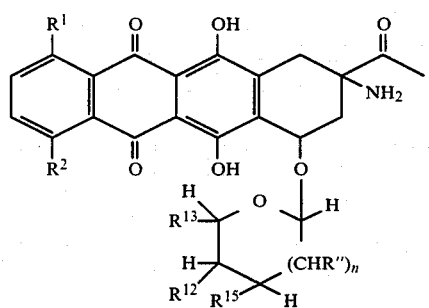

(IX)

wherein R'', $R^1$, $R^2$, $R^{11}$, $R^{12}$, $R^{13}$ and n are as defined above; and $R^{15}$ is a hydrogen atom, hydroxy group, amino group or halogen-substituted lower alkanoylamino group; to react with trifluoroacetic acid anhydride in a solvent such as dichloromethane, chloroform, tetrahydrofuran, etc., in the presence of a base such as triethylamine, pyridine, etc., followed by addition of a mixture of (1) methanol or hydrous methanol with (2) triethylamine or sodium hydrogen carbonate until partial trifluoroacetylation of only amino group in the molecule is selectively effected.

A reaction of a compound having the formula (XI) with a compound having the formula (XII) in a solvent such as dimethylformamide, dimethylsulfoxide, tetrahydrofuran, diglyme, etc., in the presence of tertiary amine such as triethylamine, dimethylaniline, etc., produces a compound having the formula (XIII):

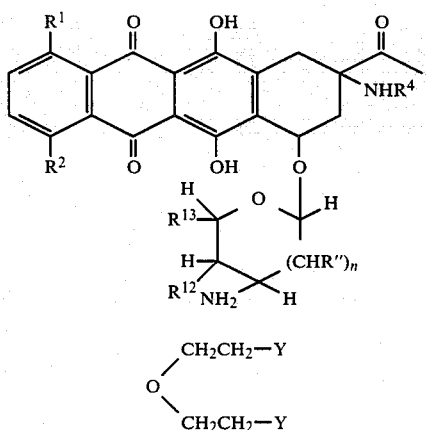

(XI)

(XII)

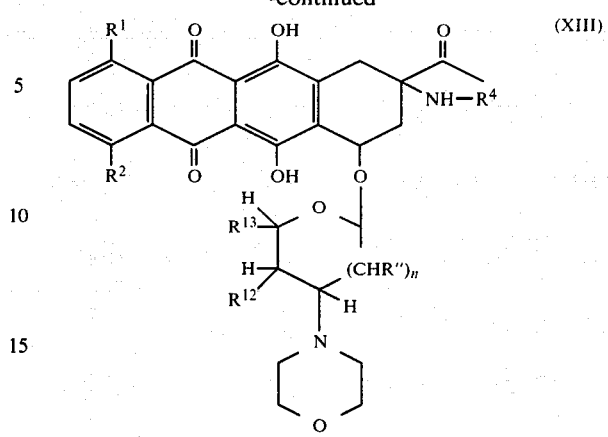

(XIII)

wherein R'', $R^1$, $R^2$, $R^4$, $R^{12}$, $R^{13}$ and n are as defined above; and Y is a bromine atom or an iodine atom.

A reaction of a compound having the formula (XIV) with dihydropyran in an anhydrous solvent such as toluene, acetonitrile, dimethylformamide, etc., in the presence of an acid catalyst such as p-toluenesulfonic acid; benzenesulfonic acid, produces a compound having the formula (XV):

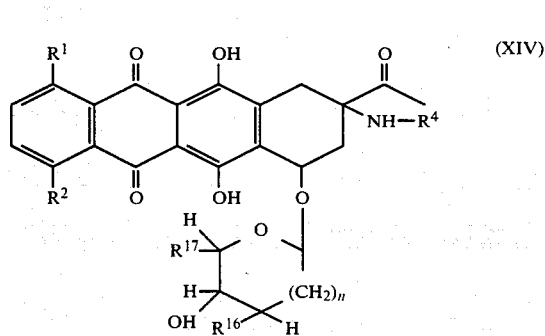

(XIV)

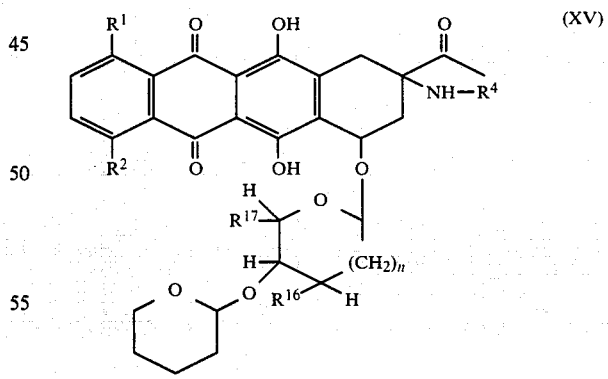

(XV)

wherein $R^1$, $R^2$, $R^4$ and n are as defined above; $R^{16}$ is a hydrogen atom, amino group, or halogen-substituted lower alkanoyl amino group; and $R^{17}$ is a hydrogen atom or methyl group.

Reduction of the compound having the formula (XVI) obtained according to the procedure above, until 13-oxo group is reduced, produces a compound having the formula (XVII):

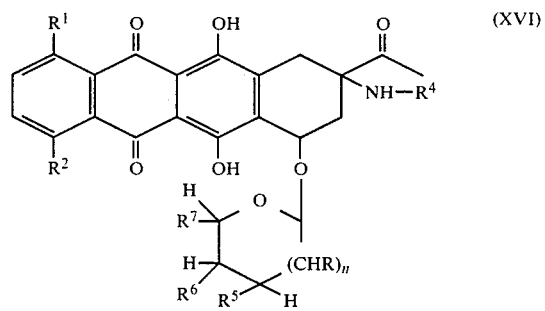

(XVI)

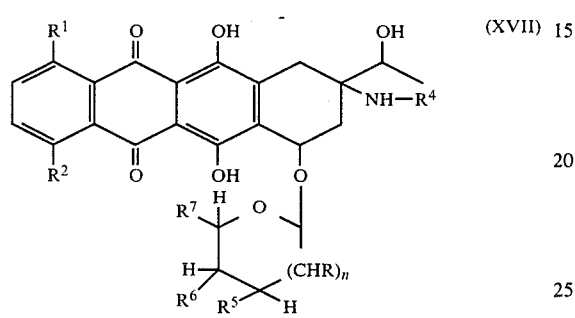

(XVII)

wherein R, $R^1$, $R^2$, $R^4$, $R^5$, $R^6$, $R^7$ and n are as defined above. The reduction may be carried out with a reducing agent which is capable of reducing oxo-group, such as a boron-containing reducing agent, e.g., sodium cyanoborohydride, lithium cyanoborohydride, or sodium borohydride, or an aluminum-containing reducing agent, e.g., lithium aluminum hydride, diisobutylaluminum hydride, sodium diethyl dihydro aluminate. Boron-containing reducing agent is preferred when ester group and amido group are present in the molecule. The reduction is carried out in such a solvent as water, methanol, ethanol, isopropyl alcohol, tetrahydrofuran, dioxane or a mixture thereof at a temperature of from −20° C. to 40° C., when the boron-containing reducing agent is employed. On the other hand, the reduction is carried out in a solvent such as tetrahydrofuran, dioxane, diethyl ether, etc., at a temperature of from −100° C. to −20° C., when the aluminum-temperature containing reducing agent is employed.

Compound (A) having the formula (XVII) and having an amido linkage in the molecule is obtained by reduction of oxo group of the corresponding compound having the formula (XVI) in the manner mentioned above. Alternatively, the compound (A) above is obtained by amidation of a compound having the formula (XVII) and having amino group, until the amino group is converted into amido group. On the other hand, a compound having the formula (XVII) and having amino group in the molecule may also be obtained by hydrolysis of a compound having the formula (XVII) and having trifluoroacetamido group in the molecule.

A compound having the formula (II) wherein both $R^1$ and $R^2$ are hydrogen atoms, which is the starting compound of the present invention, is prepared according to processes disclosed in EPC Publication No. 72259 published on Feb. 16, 1983. A compound wherein either $R^1$ or $R^2$ is a hydrogen atom and the other is methoxy group or hydroxy group, which is new, is prepared according to the reaction scheme mentioned below:

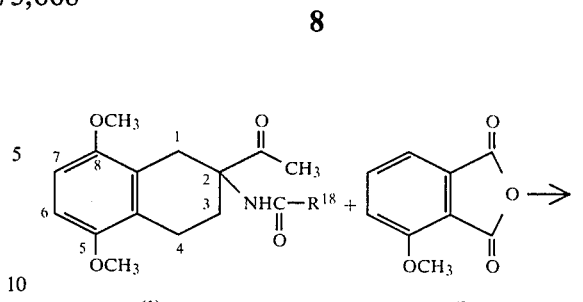

(1)     (2)

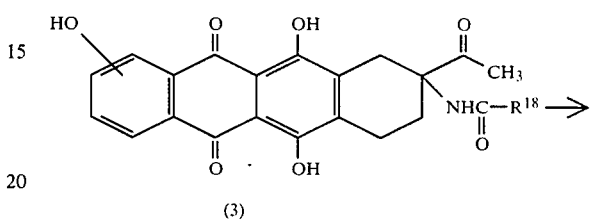

(3)

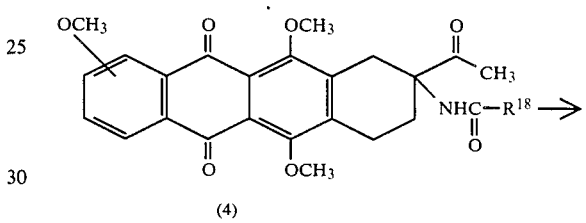

(4)

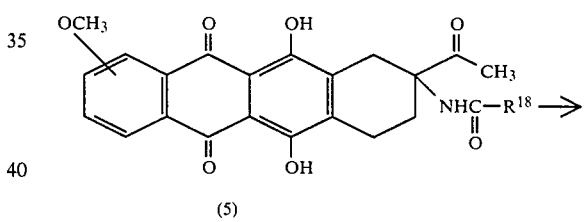

(5)

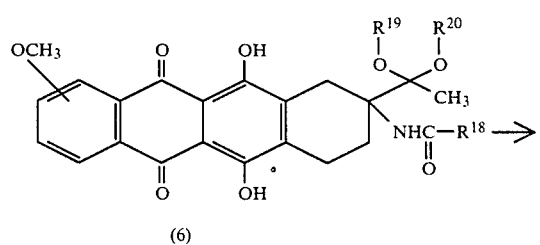

(6)

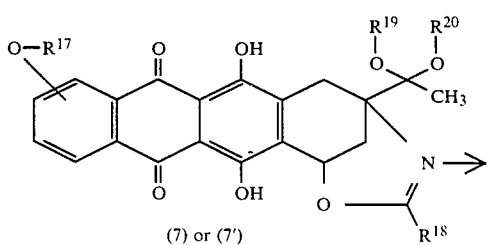

(7) or (7')

where (7) $R^{17}$ = $CH_3$
(7') $R^{17}$ = H

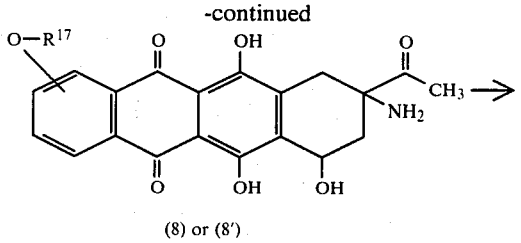

(8) or (8')

where (8) $R^{17} = CH_3$
(8') $R^{17} = H$

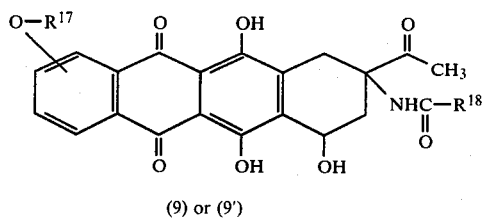

(9) or (9')

where (9) $R^{17} = CH_3$
(9') $R^{17} = H$ wherein $R^{17}$ is as defined above; $R^{18}$ is lower alkyl group or halogenated lower alkyl group ($C_{1-3}$ alkyl group); $R^{19}$ and $R^{20}$ are both methyl groups or ethyl groups or, when taken together represent an ethylene group; and hydroxy or methoxy group in the formulas (3), (4), (5), (6), (7), (7'), (8), (8'), (9), (9') locates at 1- or 4-position.

As illustrated above, compound (1) is allowed to react with derivative of phthalic anhydride (2) in the presence of a Lewis acid such as aluminum chloride to obtain a compound (3). Conversion of phenolic hydroxy group of the compound (3) into methoxy group as in the compound (4) is made by use of a compound such as dimethylsulfate. Treatment of the compound (4) with a compound such as aluminum chloride provides a compound (5). Protection of the ketone group of the compound (5) is made by the manner familiar to the skilled to obtain a compound (6) which is then allowed to react with a halogenating agent such as N-bromo succinic acid amide to produce a compound (7) wherein $R^{17}$=CH$_3$. Hydrolysis of the compound (7) with an acid such as hydrochloric acid produces a compound (8) where $R^{17}$ is methyl group, and, if necessary, the methyl group is converted into a hydrogen atom by use of a compound such as aluminum chloride. Treatment of the compound (7) with a compound such as aluminum chloride gives a compound (7') where $R^{17}$ is a hydrogen atom. Hydrolysis of the compound (7') with an acid such as hydrochloric acid gives the compound (8') where $R^{17}$ is a hydrogen atom. If necessary, acylation of the compound (8) or (8') gives a compound (9) or (9'), respectively.

Compound (3) produced from a reaction between compounds (1) and (2) has two positional isomers depending on position of the hydroxy group. Compounds (4), (5), (6), (7), (7'), (8), (8'), (9) and (9') also have the same isomers. It is possible to separate these isomers from each other by chromatography or others in any of the compounds (3)–(9) and (9'), but preferably in compound (5) or (7), more preferably in compound (5) by fractional crystallization.

Optically active forms of the compounds (8) and (9) are obtained as in the same scheme above when optically active form of the compound (1) is used. Racemic and optically active compound (1) are obtained in accordance with the procedure described in EPC Publication No. 72259 published on Feb. 16, 1983. A compound having the formula (II) wherein both $R^1$ and $R^2$ are hydrogen atoms is also obtained as in the same procedure as above.

Aminonaphthacene derivative having the formula (I) of the present invention consists of a sugar component and an aglycone component. The steric configuration of the compound (I) is as follows.

Preferable sugar component of the compound (I) is 2,6-dideoxy-L and D-lyxo-hexopyranose derivative, 3-amino-2,3,6-trideoxy-L and D-lyxo-hexopyranose derivative, 2,6-dideoxy-L and D-arabino-hexopyranose derivative, 2,3,6-trideoxy-L and D-erythro-hexopyranose derivative, 2,3,6-trideoxy-L and D-galacto-hexopyranose derivative, 2-deoxy-L and D-arabino-hexopyranose derivative, 3-amino-2,3,6-trideoxy-L and D-arabino-hexopyranose derivative, 3-amino-2,3,4,6-tetradeoxy-L and D-threo-hexopyranose derivative, 2-deoxy-L and D-erythro-pentapyranose derivative, 2-deoxy-L and D-threo-pentapyranose derivative, tetrahydropyranyl, and tetrahydrofuranyl.

The sugar component forms 1'α- or 1'β-combination with the aglycone component.

The aglycone component is illustrated by planar structural formulas wherein there are asymmetric carbon atoms at 7- and 9-positions, and, in some cases, at 13-position, too. The present compound includes all steric isomers based on these asymmetric carbon atoms. Stereo-configuration of the aglycone component, preferable from a view point of an anti-tumor activity, is that the oxygen atom at 7-position and the nitrogen atom at 9-position define cis-coordination, more preferably, stereoconfiguration at 9-position of aglycone is the same as that of 2-position of l-isomer of a compound (1) in the scheme above where $R^{18}$ is methyl group.

The preparation of pharmaceutical compositions can be carried out by a conventional method, for example, the aminonaphthacene derivatives (I), they may be mixed with carriers, diluents, lubricants, fillers and/or binders such as lactose, sucrose, calcium, phosphate, starch, talcum, casein, magnesium stearate, methyl cellulose, polyglycols, tragacanth and the like, sometimes together with stabilizers and emulsifying agents. The resulting mixture may be processed in a usual manner to tablets, capsules, pills, ampoules and the like.

EXAMPLE 1

In 20 ml of dichloromethane was dissolved 305 mg of d-9α-amino-9β-acetyl-7,8,9,10-tetrahydro-6,7β,11-trihydroxy-5,12-naphthacenedione $[[\alpha]_D^{25}+153°$ (C=0.06, chloroform), hydrochloride: $[\alpha]_D^{20}31$ 89° (c=0.1, DNF)]. To this solution was added 400 mg of Molecular Sieves 4A and then this was cooled to 5° C. or lower. To the solution were added a solution of 3,4-di-0-acetyl-2,6-dideoxy-α-L-lyxo-hexopyranosyl chloride (521 mg) in dichloromethane (10 ml) and a solution of silver trifluoromethanesulfonate (540 mg) in diethyl ether (10 ml) and reaction was carried out at 5° C. or lower for 1 hour. To the reaction mixture were added 100 ml dichloromethane and 30 ml of a saturated aqueous sodium bicarbonate solution. Then, insoluble materials were eliminated by filtration and the organic layer was separated, washed with water, dried over magnesium sulfate and then concentrated under reduced pressure to obtain 764 mg of a residue. This residue was purified by silica gel chromatography (eluant: 5% methanol/chloroform) to obtain 344 mg of d-7α-[(3,4-di-0-acetyl-2,6-dideoxy-α-L-lyxo-hexopyranosyl)oxy]-9α-amino-9β-acetyl-7,8,9,10-tetrahydro-6,11-dihydroxy-5,12-naphthacenedione [m.p. 155°–157° C.; $[\alpha]_D^{27} + 171°$ (c=0.21, chloroform)].

EXAMPLE 2

120 mg of d-7α-[3,4-di-0-acetyl-2,6-dideoxy-α-L-lyxo-hexopyranosyl)oxy]-9α-amino--acetyl-7,8,9,10-tetrahydro-6,11-dihydroxy-5,12-naphthacenedione obtained in Example 1 was dissolved in 12 ml of methanol and 12 ml of tetrahydrofuran. Then, to the solution was added 232 mg of potassium carbonate while cooling with ice water and reaction was effected at this temperature for 1 hour. The reaction mixture was made acidic with 3% aqueous hydrochloric acid solution, then alkaline by adding 20 ml of a saturated aqueous sodium bicarbonate solution and was extracted with dichloromethane. The organic layer was washed with a saturated aqueous sodium chloride solution and then dried over magnesium sulfate, followed by removal of the solvent by distillation under reduced pressure to obtain 91 mg of residue. This residue was purified by a silica gel column chromatography (eluant: 10% methanol/chloroform) to obtain 81 mg of d-7α-[(2,6-dideoxy-α-L-lyxo-lexopyranosyl)oxy]-9α-amino-9β-acetyl-7,8,9,10-tetrahydro-6,11-dihydroxy-5,12-naphthacenedione [m.p. 178°–182° C.; $[\alpha]_D^{27} + 871°$ (c=0.16, chloroform)].

EXAMPLE 3

324 mg of d-9β-acetyl-9α-trifluoroacetylamino-7,8,9,10-tetrahydro-6,7α,11-trihydroxy-5,12-naphthacenedione [$[\alpha]_D^{25} + 207°$ (c=0.2, chloroform)] was dissolved in 15 ml of dichloromethane. To this solution was added 550 mg of Molecular Sieves 4A and this was cooled with ice water. To this solution was added a solution of 800 mg of 3,4-di-0-acetyl-2,6-dideoxy-α-L-lyxo-hexopyranosyl chloride in 5 ml of dichloromethane and then was added a solution of 540 mg of silver trifluoromethane sulfonate in 6 ml of diethyl ether and reaction was carried out for 45 minutes while cooling with ice water. To the reaction mixture were added 50 ml of dichloromethane and 20 ml of a saturated aqueous sodium bicarbonate solution. Insoluble materials were removed by filtration and thereafter the organic layer was separated, washed with saturated aqueous sodium chloride solution and dried with magnesium sulfate, followed by removal of the solvent by distillation under reduced pressure to obtain a residue. This residue was purified by a silica gel column chromatography (eluant: 1% methanol/chloroform) to obtain 78 mg of d-7α-[(3,4-di-0-acetyl-2,6- dideoxy-α-L-lyxo-hexopyranosyl)oxy]-9β-acetyl-9α-trifluoroacetamide-7,8,9,10-tetrahydro-6,11-dihydroxy-5,12-naphthacenedione [m.p. 130°–140° C.; $[\alpha]_D^{27} + 226°$ (c=0.16, chloroform)].

EXAMPLE 4

80 mg of d-7α-[(3,4-di-0-acetyl-2,6-dideoxy-α-L-lyxo-hexopyranosyl)oxy]-9α-amino-9β-acetyl-7,8,9,10-tetrahydro-6,11-dihydroxy-5,12-naphthacenedione obtained in Example 1 was dissolved in 10 ml of dichloromethane. Then, to the resultant solution were added 170 mg of pyridine and 180 mg of trifluoroacetic anhydride while cooling with ice water and reaction was carried out at room temperature for 1 hour. After reaction, to the reaction mixture were added 20 ml of methanol and 20 ml of a saturated aqueous sodium bicarbonate solution and reaction was carried out at room temperature for 1 hour. Thereafter, extraction was effected with 100 ml of dichloromethane to obtain 91 mg of d-7α-[(3,4-di-0-acetyl-2,6-dideoxy-α-L-lyxo-hexopyranosyl)oxy]-9β-acetyl-9α-trifluoroacetamide-7,8,9,10-tetrahydro-6,11-dihydroxy-5,12-naphthacenedione (m.p. 133°–140° C.).

EXAMPLE 5

In 36 ml of dichloromethane was dissolved 294 mg of d-9α-amino-9β-acetyl-7,8,9,10-tetrahydro-6,7α,11-trihydroxy-5,12-naphthacenedione [$[\alpha]_D^{25} + 153°$ (c=0.06, chloroform); hydrochloride: $[\alpha]_D^{20} - 89°$ (c=0.1, DMF)] and 550 mg of Molecular Sieves 4A was added thereto. Then, the solution was cooled with ice water. Thereto were added a solution of 600 mg of 2,3,6-trideoxy-3-trifluoroacetamide-4-0-trifluoroacetyl-α-L-lyxo-hexopyranosyl chloride in 8 ml of dichloromethane and a solution of 510 mg of silver trifluoromethansulfonate in 8 ml of diethyl ether, followed by reacting for 1 hour while cooling with ice water. To the reaction mixture were added 50 ml of methanol and 10 ml of a saturated aqueous sodium bicarbonate solution and this mixture was stirred for 1 hour while cooling with ice water, followed by addition of 200 ml of dichloromethane, removal of insoluble materials by filtration and separation of the organic layer. This organic layer was washed with water and concentrated to obtain a residue, which was then purified by a silica gel column chromatography (eluant: 5% methanol/chloroform) to obtain 347 mg of d-7α-[(2,3,6-trideoxy-3-trifluoroacetamide-α-lyxo-hexopyranosyl)oxy]-9α-amino-9β-acetyl-7,8,9,10-tetrahydro-6,11-dihydroxy-5,12-naphthacenedione [m.p. 143°–145° C.; $[\alpha]_D^{25} + 184°$ (c=0.12, chloroform)]. This product was converted to a hydrochloride by the conventional method which had a melting point of 173°–174° C.

EXAMPLE 6

In 12 ml of methanol was dissolved 80 mg of d-7α-[(2,3,6-trideoxy-3-trifluoroacetamide-α-L-lyxo-hexopyranosyl)oxy]α9-amino-9β-acetyl-7,8,9,10-tetrahydro-6,11-dihydroxy-5,12-naphthacenedione obtained in Example 5. To the resultant solution was added 5 ml of 10% aqueous potassium carbonate solution while cooling with ice water and reaction was effected at this temperature for 12 hours. The reaction mixture was acidified by adding 3% aqueous hydrochloric acid solution and thereafter made alkaline with a saturated aqueous sodium bicarbonate solution and was extracted with chloroform. A residue obtained by the extraction was purified by a silica gel column chromatography (eluant: 5% methanol/chloroform containing 0.5% aqueous ammonia) and then was converted to a hydrochloride by a conventional method to obtain 24 mg of d-7α[(2,3,6-trideoxy-3-amino-α-L-lyxo-hexopyranosyl)oxy]-9α-amino-9β-acetyl-7,8,9,10-tetrahydro-6,11-dihydroxy-5,12-naphthacenedione dihydrochloride [m.p. 176°–180° C.; $[\alpha]_D^{25} + 149°$ (c=0.11, water)].

Example 7

Reaction and after-treatments were carried out in the same manner as in Example 4 using 60 mg of d-7α-(2,3,6-trideoxy-3-trifluoroacetamide-α-L-lyxo-hexopyranosyl)oxy]-9α-amino-9β-acetyl-7,8,9,10-tetrahydro-6,11-dihydroxy-5,12-naphthacenedione obtained in Example 5. There was obtained 47 mg of d-7α-[(2,3,6- trideoxy-3-trifluoroacetamide-α-L-lyxo-hexopyranosyl)oxy]-9β-acetyl-9α-trifluoroacetamide-7,8,9,10-tetrahydro-6,11-dihydroxy-5,12-naphthacenedione [m.p. 175°–177° C.; $[\alpha]_D^{27}+246°$ (c=0.1, chloroform)].

EXAMPLE 8

Reaction was carried out in the same manner as in Example 1 using 305 mg of 1-9α-amino-9β-acetyl-7,8,9,10-tetrahydro-6,7α,11-trihydroxy-5,12-naphthacenedione $[\alpha]_D^{25}-143°$ (c=0.07, chloroform); hydrochloride: $[\alpha]_D^{20}+87°$ (c=0.1, DMF)]. There was obtained 365 mg of l-7α-[(3,4-di-0-acetyl-2,6-dideoxy-α-L-lyxo-hexopyranosyl)oxy]-9α-amino-9β-acetyl-7,8,9,10-tetrahydro-6,11-dihydroxy-5,12-naphthacenedione as an oily material. 265 mg of this oily material was dissolved in chloroform, followed by adding thereto hydrogen chloride/ether to obtain 234 mg of a hydrochloride of said compound [m.p. 171°–174° C.; $[\alpha]_D^{25}-258°$ (c=0.11, water)].

EXAMPLE 9

Reaction was carried out in the same manner as in Example 4 using 100 mg of 7α-[(3,4-di-0-acetyl-2,6-dideoxy α-L-lyxo-hexopyranosyl)oxy]-9α-amino-9β-acetyl-7,8,9,10-tetrahydro-6,11-dihydroxy-5,12-naphthacenedione obtained in Example 8. There was obtained 93 mg of 1-7α-[(3,4-di-0-acetyl-2,6-dideoxy-α-L-lyxo-hexopyranosyl)oxy]-9β-acetyl-9α-trifluoroacetamide-7,8,9,10-tetrahydro-6,11-dihydroxy-5,12-naphthacenedione [m.p. 161°–165° C.; $[\alpha]_D^{27}-415°$ (c=0.12, chloroform)].

EXAMPLE 10

1.0 g of 1-9α-amino-9β-acetyl-7,8,9,10-tetrahydro-6,7α,11-trihydroxy-5,12-naphthacenedione hydrochloride [[α]$_D^{20}$ –89° (c=0.1, DMF)] was dissolved in 10 ml of dimethylformamide, followed by adding 3 ml of dihydropyran and 10 mg of anhydrous p-toluensulfonic acid. The mixture was stirred at room temperature overnight. To the reaction mixture was added 100 ml of methylene chloride and thereafter the reaction mixture was washed three times with 50 ml of a saturated aqueous sodium bicarbonate solution and a saturated sodium chloride solution. The organic layer was dried with sodium sulfate and then concentrated under reduced pressure to obtain 1.5 g of a residue. This residue was purified by a silica gel column chromatography (eluant: 5% methanol/chloroform) to obtain two kinds of 7-0-tetrahydropyranyl-9α-amino-9β-acetyl-7,8,9,10-tetrahydro-6,7α,11-trihydroxy-5,12-naphthacenedione (abbreviated as 7-THP hereinafter) which were diastereomers.

7-THP-A: Rf 0.24 (silica gel, 5% methanol/chloroform); m.p. 155°–159° C.; $[\alpha]_D^{30}+84.7°$ (c=0.10, chloroform).

7-THP-B: Rf 0.19 (silica gel, 5% methanol/chloroform); m.p. 120°–126° C.; $[\alpha]_D^{30}+231°$ (c=0.11, chloroform).

EXAMPLE 11

In 20 ml of dry dichloromethane was dissolved 184 mg (0.5 mmol) of d-9α-amino-9β-acetyl-7,8,9,10-tetrahydro-6,7α,11-trihydroxy-5,12-naphthacenedione [[α]$_D^{25}$+153° (c=0.06, chloroform)] and 368 mg of powdered Molecular Sieves 4A were added thereto, followed by cooling it to 5° C. or lower. To this solution were added a solution of 590 mg 2-deoxy-3,4-di-0-acetyl-D-erythro-pentapyranosyl chloride in 10 ml of dry dichloromethane and a solution of 707 mg of silver trifluoromethanesulfonate in 8 ml of dry diethyl ether and reaction was effected at 5° C. or lower for 2 hours. To the reaction mixture were added 100 ml of dichloromethane and 30 ml of a saturated aqueous sodium bicarbonate solution, followed by removal of insoluble materials by filtration and separation of the organic layer. The organic layer was washed with water and a saturated aqueous sodium chloride solution, then dried with sodium sulfate and concentrated under reduced pressure to obtain 700 mg of a residue. This residue was purified by a silica gel chromatography (eluant: 5% methanol/dichloromethane) to obtain 150 mg of d-7α-[(2-deoxy-3,4-di-0-acetyl-β-D-erythro-pentapyranosyl)oxy]-9α-amino-9β-acetyl-7,8,9,10-tetrahydro-6,11-dihydroxy-5,12-naphthacenedione [m.p. 141°–143° C.; $[\alpha]_D^{20}+120°$ (c=0.1, chloroform); IR(Nujol)ν: 1740, 1705, 1620, 1590 cm$^{-1}$; NMR(CDCl$_3$)δ: 1.97(3H, S), 2.13(3H, S), 2.36(3H, S), 3.03 (2H, bs), 4.05(2H, q), 4.90–5.33(3H, m), 5.50(1H, bs) 7.70–7.93(2H, m), 8.20–8.46(2H, m); Mass Spectrometric Analysis (abbreviated as "MS" hereinafter): [M]+568]. Hydrochloride of this compound had a melting point of 59°–161° C.

EXAMPLE 12

Three hundred mg (0.53 mmol) of d-7α-[(2-deoxy-3,4-di-0-acetyl-β-D-erythro-pentapyranosyl)oxy]-9α-amino-9β-acetyl-7,8,9,10-tetrahydro-6,11-dihydroxy-5,12-naphthacenedione obtained in Example 11 was added to a solution of 290 mg of potassium carbonate in 15 ml of dry tetrahydrofuran and 15 ml of dry methanol and reaction was carried out at room temperature for 30 minutes with stirring. The reaction mixture was made weakly acidic with 1N-hydrochloric acid and then adjusted to pH 8 with a saturated aqueous sodium bicarbonate solution. Then, the reaction mixture was extracted with dichloromethane (150 ml×4) and the organic layer was washed with water and a saturated aqueous sodium chloride solution and dried with sodium sulfate. After concentration under reduced pressure, the resultant residue was crystallized from dichloromethane-methanoldiethyl ether to obtain 130 mg of d-7α-[(2-deoxy-β-D-erythro-pentapyranosyl)oxy]-9αamino-9β-acetyl-7,8,9,10-tetrahydro-6,11-dihydroxy-5,12-naphthacenedione [m.p. 174°–178° C.; JR(Nujol)ν: 1710, 1620, 1590 cm$^{-1}$; NMR(CDCl$_3$)δ: 1.70–2.30(4H, m), 2.30(3H, S), 3.00(2H, S), 3.57–3.83 (2H, m), 4.96(1H, bs), 5.33(1H, S), 7.80–8.00(2H, m), 8.15–8.36(2H, m); MS: [M+1]+ 484]. Hydrochloride of this compound had a melting point of 145°–151° C.

EXAMPLE 13

Reaction and after-treatments were carried out in the same manner as in Example 11 using 92 mg (0.25 mmol) of d-9α-amino-9β-acetyl-7,8,9,10-tetrahydro-6,7α,11-trihydroxy-5,12-naphthacenedione and 236 mg of 2-deoxy-3,4-di-0-acetyl-L-erythro-pentapyranosyl chloride. The resultant residue was purified by a silica gel chromatography (eluant: 5% methanol/dichloromethane) to obtain 63 mg of d-7α-[(2-deoxy-3,4-di-0-acetyl-β-L-erythropentapyranosyl)oxy]-9α-amino-9β-acetyl-7,8,9,10-tetrahydroxy-6,11-dihydroxy-5,12-naphthacenedione as a jelly material [NMR(CDCl$_3$)δ: 1.97(3H, S), 2.17(3H, S), 2.40 (3H, S), 3.06(2H, bs), 4.13(2H, q), 5.00–5.40(3H, m), 5.43(1H, bs), 7.69–7.90(2H, m), 8.10–8.30(2H, m); MS: [M]+ 568; IR(Nujol)ν: 1740, 1630, 1590 cm$^{-1}$]. Hydrochloride of this compound had a melting point of 145°–148° C.

EXAMPLE 14

Reaction and after-treatments were carried out in the same manner as in Example 11 using 184 mg (0.5 mmol) of d-9α-amino-9β-acetyl-7,8,9,10-tetrahydro-6,7α,11-trihydroxy-5,12-naphthacenedione and 752 mg of 2,6-dideoxy-3,4-di-0-acetyl-L-arabino-hexopyranosyl chloride. The resultant residue obtained was purified by a silica gel chromatography (eluant: 10% methanol/dichloromethane) to give 100 mg of d-7α-[(2,6-dideoxy-3,4-di-0-acetyl-α-L-arabinohexopyranosyl)oxy]-9α-amino-9β-acetyl-7,8,9,10-tetrahydro-6,11-dihydroxy-5,12-naphthacenedione [m.p. 112°–120° C.; IR(Nujol)ν: 1730, 1700, 1620, 1580 cm$^{-1}$; NMR(CDCl$_3$)δ: 1.25(3H, d), 1.96(3H, S), 2.06(3H, S), 2.42(3H, S), 1.60–2.30(4H, m), 3.07(2H, S), 4.00–4.35(1H, m), 4.80(1H, t), 4.97–5.23(2H, m), 5.50(1H, bs), 7.76–7.97(2H, m), 8.23–8.50(2H, m); MS: [M+1]$^+$ 583]. Hydrochloride this compound had a melting point of 144°–151° C.

EXAMPLE 15

Reaction and after-treatments were carried out in the same manner as in Example 11 using 184 mg (0.5 mmol) of d-9α-amino-9β-acetyl-7,8,9,10-tetrahydro-6,7α,11-trihydroxy-5,12-naphthacenedione and 752 mg of 2,6-dideoxy-3,4-0-acetyl-D-lyxo-hexopyranosyl chloride. The residue obtained was purified by a silica gel chromatography (eluant: 10% methanol/dichloromethane) to provide 118 mg of d-7α-[(2,6-dideoxy-3,4-di-0-acetyl-α-D-lyxo-hexopyranosyl) oxy]-9α-amino-9β-acetyl-7,8,9,10-tetrahydro-6,11-dihydroxy-5,12-naphthacenedione [m.p. 113°–121° C.; IR(Nujol)ν: 1735, 1705, 1620, 1580 cm$^{-1}$; NMR(CDCl$_3$)δ: 1.23(3H, d), 1.98(3H, S), 2.15(3H, S), 2.35(3H, S), 3.05(2H, bs); 5.53(1H, bs), 7.70–7.93(2H, m), 8.20–8.46(2H, m); MS: [M+1]$^+$ 583]. Hydrochloride of this compound had a melting point of 161°–165° C.

EXAMPLE 16

Reaction and after-treatments were carried out in the same manner as in Example 11 using 150 mg (0.41 mmol) of d-9α-amino-9β-acetyl-7,8,9,10-tetrahydro-6,7α,11-trihydroxy-5,12-naphthacenedione and 578 mg of 2,3,6-trideoxy-4-0-acetyl-L-erythro-hexopyranosyl chloride. The residue obtained was purified by a silica gel chromatography (eluant: 5% methanol/dichloromethane) to give 43 mg of d-7α-[(2,3,6trideoxy-4-0-acetyl-α-L-erythro-hexopyranosyl) oxy]-9α-amino-9β-acetyl-7,8,9,10-tetrahydro-6,11-dihydroxy-5,12-naphthacenedione (m.p. 176°–177° C.; IR(Nujol)ν: 1740, 1710, 1620, 1590 cm$^{-1}$; NMR(CDCl$_3$)δ: 1.20(3H, d), 1.60–2.40 (6H, m), 2.03(3H, S), 4.10(1H, m), 4.50(1H, m), 5.10(1H, bs), 5.33(1H, bs), 7.70–7.90(2H, m), 8.20–8.46(2H, m); MS: [M]$^+$ 524]. Hydrochloride of this compound had a melting point of 157°–163° C.

EXAMPLE 17

Reaction and after-treatments were carried out in the same manner as in Example 11 using 184 mg (0.5 mmol) of d-9α-amino-9β-acetyl-7,8,9,10-tetrahydro-6,7α,11-trihydroxy-5,12-naphthacenedione and 617 mg of 6-deoxy-2,3,4-tri-0-acetyl-L-galacto-hexopyranosyl chloride. The resultant residue obtained was purified by a silica gel chromatography (eluant: 10% methanol/dichloromethane) to give 50 mg of d-7α-[(6-deoxy-2,3,4-tri-0-acetyl-α-L-galactohexopyranosyl)oxy]-9α-amino-9β-acetyl-7,8,9,10-tetrahydro-5,12-naphthacenedione [m.p. 74°–82° C.; IR(Nujol)ν: 1730, 1620, 1580 cm$^{-1}$; NMR(CDCl$_3$)δ: 1.43(3H, d), 2.00(3H, S), 2.15(6H,S), 2.40(3H, S), 1.80–2.20(2H, m), 2.80–3.17(3H, m) 4.37–4.50(1H, m), 4.90–5.40(4H, m), 7.73–7.90(2H, m), 8.20–8.43 (2H, m); MS: [M]$^+$ 640]. Hydrochloride of this compound had a melting point of 157°–172° C.

EXAMPLE 18

Reaction and after-treatments were carried out in the same manner as in Example 11 using 184 mg (0.5 mmol) of d-7α-amino-9β-acetyl-5,7,8,9,10,12-hexahydro-6,7α,11-trihydroxy-5,12-naphthacenedione and 920 mg of 2-deoxy-3,4,6-tri-0-acetyl-L-arabino-hexopyranosyl chloride. Then, the resultant residue obtained was purified by a silica gel chromatography (eluant: 5% methanol/dichloromethane) to provide 32 mg of d-7α-[(2-deoxy-3,4,6-tri-0-acetyl-α-L-arabino-hexopyranosyl)oxy]-9α-amino-9β-acetyl-7,8,9,10-tetrahydro-6,11-dihydroxy-5,12-naphthacenedione [m.p. 108°–112° C.; IR(Nujol)ν: 1740, 1710, 1625, 1590 cm$^{-1}$; NMR(CDCl$_3$)δ: 1.98(3H, S), 2.00(3H, S), 2.13(3H, S), 2.40 (3H, S), 3.10(2H, S), 4.06–4.50(3H, m), 4.90–5.30(3H, m), 5.56(1H, m), 7.80–8.00(2H, m), 8.26–8.50(2H, m); MS: [M]$^+$ 640]. Hydrochloride of this compound had a melting point of 145°–147° C.

EXAMPLE 19

200 mg of d-4-methoxy-9α-amino-9β-acetyl-6,7α,11-trihydroxy-7,8,9,10-tetrahydro-5,12-naphthacenedione [[α]$_D^{20}$ +113° (c=0.1, CHCl$_3$)] was dissolved in 40 ml of dichloromethane. To this solution was added 400 mg of Molecular Sieves 4A and then the solution was cooled to 5° C., followed by adding thereto a solution of 2-deoxy-3,4-di-0-acetyl-D-erythro-pentopyranosyl chloride (596 mg) in dichloromethane (15 ml) and a solution of silver trifluoromethanesulfonate (712 mg) in diethyl ether (10 ml) and reacting at 5° C. or lower for 1 hour. To the reaction mixture were added 100 ml of dichloromethane and 30 ml of a saturated sodium bicarbonate solution, then insoluble materials were removed by filtration and the organic layer was separated. This organic organic layer was washed with water, dried over sodium sulfate and thereafter concentrated under reduced pressure to obtain 820 mg of a residue. This residue was purified by a silica gel column chromatography (eluant: 3% methanol/dichloromethane) to obtain a reddish orange crystal of d-7α-[(2-deoxy-3,4-di-0-acetyl-8-D-erythro-pentapyranosyl)oxy]-4-methoxy-9α-amino-9β-acetyl-6,11-dihydroxy-7,8,9,10-tetrahydro-5,12-naphthacenedione [m.p. 122°–124° C. IR(Nujol)$^{cm-1}$: 3300–3600, 1740, 1610, 1580; MS: [M+1]$^+$ 598; [α]$_D^{20}$+151.2° (c=0.1, CHCl$_3$)]. Hydrochloride of this compound had a melting point of 173°–175° C.

EXAMPLE 20

Ninety five mg of d-4-methoxy-9α-amino-9β-acetyl-6,7α,11-trihydroxy-7,8,9,10-tetrahydro-5,12-naphthacenedione [[α]$_D^{20}$ +113° (c=0.1, CHCl$_3$) was dissolved in 19 ml of dichloromethane. To this solution was added 190 mg of Molecular Sieves 4A, followed by cooling with ice water. Thereto were added a solution of 2,3,6-trideoxy-3-trifluoroacetamide-4-0-trifluoroacetyl-L-lyxo-hexopyranosyl chloride (429 mg) in dichloromethane (6 ml) and a solution of silver trifluoromethane-sulfonate (340 mg) in diethyl ether (8 ml) and reaction was carried out for 1 hour while cooling with ice water. To the reaction mixture were added 100 ml of dichloromethane and 20 ml of a saturated aqueous sodium bicarbonate solution, then insoluble materials were removed by filtration and the organic layer was separated. This organic layer was washed with water, dried over sodium sulfate and concentrated under reduced pressure to obtain 650 mg of a residue. This residue was purified by a silica gel column chromatography (eluant: 5% methanol/dichloromethane) to obtain d-7α-[(2,3,6-trideoxy-3-trifluoroacetamide-α-L-lyxo-hexopyranosyl)oxy]-4-methoxy-9α-amino-9β-acetyl-6,11-dihydroxy-7,8,9,10-tetrahydro-5,12-naphthacenedione [m.p. 155°–157° C.; MS: [M+1]+ 623, [a]$_D^{20}$+243.8° (c=0.1, CHCl$_3$)].

EXAMPLE 21

In 5 ml of methanol was dissolved 80 mg of d-7α-[(2,3,6-trideoxy-3-trifluoroacetamide-α-L-lyxo-hexopyranosyl) oxy]-4-methoxy-9α-amino-9β-acetyl-6,11-dihydroxy-7,8,9,10-tetrahydro-5,12-naphthacenedione obtained in Example 20. Thereafter, to the solution was added 5 ml of 10% aqueous potassium carbonate solution while cooling with ice water and reaction was effected at this temperature for 12 hours. The reaction mixture was poured into a 2% aqueous hydrochloric acid solution to render it acidic and then made alkaline with a saturated aqueous sodium bicarbonate solution. Sodium chloride was added to saturate the reaction mixture therewith, followed by extraction with chloroform. Thus residue obtained was purified by a silica gel column chromatography (eluant: 5% methanol/dichloromethane containing 0.5% aqueous ammonia) to give d-7α-[(2,3,6-trideoxy-3-amino-α-L-lyxo-hexopyranosyl)oxy]-4-methoxy-9α-amino-9β-acetyl-6,11-dihydroxy-7,8,9,10-tetrahydro-5,12-naphthacenedione [MS: [M+1]+ 527]. Hydrochloride of this compound had a melting point of 197°–200° C. and [α]$_D^{20}$ +148.1° (c=0.1, methanol).

EXAMPLE 22

Reaction and after-treatments were carried out in the same manner as in Example 20 using 105 mg of d-1-methoxy-9α-amino-9β-acetyl-6,7α,11-trihydroxy-7,8,9,10-tetrahydro-5,12-naphthacenedione [[α]$_D^{20}$ +123° (c=0.1, CHCl$_3$)]. There was obtained d-7α-[(2,3,6-trideoxy-3-trifluoroacetamide-α-L-lyxo-hexopyranosyl)oxy]-1-methoxy-9α-amino-9β-acetyl-6,11-dihydroxy-7,8,9,10-tetrahydro-5,12-naphthacenedione [m.p. 147°–150° C.; MS: [M+1]+623; [α]$_D^{20}$ +162.4 (c=0.1, CHCl$_3$)].

EXAMPLE 23

Reaction and after-treatments were effected in the same manner as in Example 21 using 95 mg of d-7α-[(2,3,6-trideocy-3-trifluoroacetamide-α-L-lyxo-hexopyranosyl)oxy]-1-methoxy-9α-amino-9β-acetyl-6,11-dihydroxy-7,8,9,10-tetrahydro5,12-naphtacenedione obtained in Example 22. There was obtained d-7α-[(2,3,6-trideoxy-3-amino-α-L-lyxo-hexopyranosyl)oxy]-1-methoxy-9α-amino-9β-acetyl-6,11-dihydroxy-7,8,9,10-tetrahydro-5,12-naphthaceenedione [MS: [M+1]+527]. Hydrochloride of this compound had a melting point of 198°–202° C. and [α]$_D^{20}$ +78.9° (c=0.1, methanol).

EXAMPLE 24

Reaction and after-treatments were carried out in the same manner as in Example 20 using 140 mg of d-9α-amino-9β-acetyl-4,6,7α,11-tetrahydroxy-7,8,9,10-tetrahydro-5,12-naphthacenedione. There was obtained d-7α-[(2,3,6-trideoxy-3-trifluoroacetamide-α-L-lyxo-hexopyranosyl)oxy]-9α-amino-9β-acetyl-4,6,11-trihydroxy-7,8,9,10-tetrahydro-5,12-naphthacenedione [m.p. 137°–139° C.; MS: [M+1]+609; IR(Nujol)$^{cm-1}$ 3100–3500, 1720, 1710, 1600; [α]$_D^{20}$ +286.8° (c=0.1, CHCl$_3$)].

EXAMPLE 25

Reaction and after-treatments were carried out in the same manner as in Example 21 using 20 mg of d-7α-[(2,3,6-trideoxy- 3-trifluoroacetamide-α-L-lyxo-hexopyranosyl)oxy]-9α-amino-9β-acetyl-4,6,11-trihydroxy-7,8,9,10-tetrahydro-5,12-naphthacenedione obtained in Example 24. There was obtained d-7α-[(2,3,6-trideoxy-3-amino-α-L-lyxo-hexopyranosyl)oxy]-9α-amino-9β-acetyl-4,6,11-trihydroxy-7,8,9,10-tetrahydro-5,12-naphthacenedione [m.p. 193°–197° C.; MS: [M+1]+513; [α]$_D^{20}$ +102° (c=0.06, CHCl$_3$)]. Hydrochloride of this compound had a melting point of 273°–275° C.

EXAMPLE 26

In 5 ml of dimethylformamide was dissolved 200 mg of d-4-methoxy-9α-amino-9β-acetyl-6,7α,11-trihydroxy-7,8,9,10-tetrahydro-5,12-naphthacenedione [[α]$_D^{20}$ +113° (c=0.1, CHCl$_3$)]. To the resultant solution were added 1 ml of dihydropyran and 100 mg of anhydrous p-toluenesulfonic acid and this was stirred at room temperature overnight. To the reaction mixture was added 100 ml of dichloromethane and thereafter this was washed with a saturated aqueous sodium bicarbonate solution and a saturated aqueous sodium chloride solution. The organic layer was dried over sodium sulfate and concentrated under preduced pressure to obtain 300 mg of a residue. This residue was purified by a silica gel column chromatography (eluant: 5% methanol/dichloromethane) to obtain a mixture of two kinds of 7-0-tetrahydropyranyl-4-methoxy-9α-amino-9β-acetyl-7,8,9,10-tetrahydro-6,7α,11-trihydroxy-5,12-naphthacenedione (abbreviated as 7-THP hereinafter) which were diastereomers.

7-THP-1: m.p. 138°–140° C, IR(Nujol)ν$^{cm-1}$ 3300–3600, 1740, 1620, 1585; MS: [M+1]+482.

7-THP-2: m.p. 135°–138° C., IR(Nujol)ν$^{cm-1}$ 3300–3600, 1731, 1610, 1590; MS: [M+1]+482.

EXAMPLE 27

One hundred mg of d-7α-[(3,4-di-0-acetyl-2,6-dideoxy-α-L-lyxo-hexopyranosyl)oxy]-9α-amino-9β-acetyl- 7,8,9,10-tetrahydro-6,11-dihydroxy-5,12-naphthacenedione (m.p. 155°–157° C.; [α]$_D^{27}$ +171° (c=0.21, chloroform) was dissolved in 10 ml of methanol and 5 ml of tetrahydrofuran, followed by adding 120 mg of sodium cyanoborohydride thereto and stirring at room temperature for 12 hours. Then, 120 mg of sodium cyanoborohydride was added and reaction was effected for further 4 hours. Thereafter, the reaction mixture was added to a saturated aqueous sodium bicarbonate solution and extracted three times with chloroform. The chloroform layer was washed with a saturated aqueous sodium chloride solution three times and then dried with anhydrous sodium sulfate and chloroform was removed by distillation under reduced pressure to obtain 114 mg of a residue. This residue was purified by a silica gel column chromatography (eluant: 10% methanol/chloroform) and then converted to hydrochloride with hydrochloric acid/ether to obtain 60 mg of d-7α-[(3,4-di-0-acetyl-2,6-dideoxy-α-L-lyxo-hexapyranosyl)oxy]-9α-amino-9β-(1-hydroxyethyl)-7,8,9,10-tetrahydro-6,11-dihydroxy-5,12-naphthacenedione hydrochloride [m.p. 169°–173° C.; $[\alpha]_D^{25}$ +285° (c=0.06, water)].

EXAMPLE 28

One hundred and thirty six mg of d-7α-[(2,3,4-trideoxy-3-amino-α-L-lyxo-hexopyranosyl)oxy]-9α-amino-9β-acetyl-7,8,9,10-tetrahydro-6,11-dihydroxy-5,12-naphthacenedione (m.p. 143°–145° C.; $[\alpha]_D^{25}$ +184° (c=0.12, chloroform)] was dissolved in 13 ml of methanol, 4 ml of tetrahydrofuran and 3 ml of methylene chloride. To this solution was added 168 mg of sodium cyanoborohydride and reaction was carried out at room temperature for 3 hours. Then, 168 mg of sodium cyanoborohydride was further added and reaction was carried out for further 5 hours. The same aftertreatments as in Example 27 were applied to obtain 85 mg of a residue. This residue was purified by a silica gel column chromotography (eluant: 10% methanol/chloroform containing 1% aqueous ammonia) and then converted to hydrochloride with hydrochloric acid/ether to obtain 55 mg of d-7α-[(3-amino-2,3,4-trideoxy-α-L-lyxo-hexopyranosyl)oxy]-9α-amino-9β-(1-hydroxyethyl)-7,8,9,10-tetrahydro-6,11-dihydroxy-5,12-naphthacenedione dihydrochloride [m.p. 188–191° C.; $[\alpha]_D^{25}$ +145° (c=0.06 water)].

EXAMPLE 29

Two hundred and twenty six mg of 7-THP-A obtained in the same manner as in Example 10 was dissolved in 13 ml of methanol and 4 ml of tetrahydrofuran. To the resultant solution was added 370 mg of sodium cyanoborohydride and reaction was carried out at room temperature overnight. The reaction mixture was treated in the same manner as in Example 27 and the resultant residue was purified by a silica gel column chromatography (eluant: 7% methanol/chloroform) to obtain 68 mg of 7-0-tetrahydropyranyl-9α-amino-9β-(1-hydroxyethyl)-7,8,9,10-tetrahydro-6,7α,11-trihydroxy-5,12-naphthacenedione [m.p. 112–120° C.; $[\alpha]_D^{30}$ +51.5° (c=0.13, chloroform)].

EXAMPLE 30

Reaction and the subsequent purification were carried out in the same manner as in Example 29 using 263 mg of 7-THP-B obtained in the same manner as in Example 10, to obtain 84 mg of 7-0-tetrahydropyranyl-9α-amino-9β-(1-hydroxyethyl)-7,8,9,10-tetrahydro-6,7α,11-trihydroxy-5,12-naphthacenedione [m.p. 126°–130° C.; $[\alpha]_D^{30}$ +212.2° (c=0.10, chloroform)].

EXAMPLE 31

In 16 ml of methanol was dissolved 250 mg of d-7α-[(2,3,6-trideoxy-3-trifluoroacetamide-α-L-lyxohexopyranosyl)oxy]-9α-amino-9β-acetyl-7,8,9,10-tetrahydro-6,11,-dihydroxy-5,12-naphthacenedione (m.p. 143°–145° C.; $[\alpha]_D^{25}$ +184° (c=0.12, chloroform)]. Then, to this solution was added 250 mg of sodium cyanoborohydride and reaction was carried out at room temperature for 2 days. The reaction mixture was treated and purified in the same manner as in Example 27 and then converted to hydrochloride with hydrochloric acid/ether to obtain 49 mg of d-7α-[(2,3,6-trideoxy-3-trifluoroacetamide-α-L-lyxohexopyranosyl)oxy]-9α-amino-9β-(1-hydroxyethyl)-7,8,9,10-tetrahydro-6,11-dihydroxy-5,12-naphthacenedione hydrochloride [m.p. 181°–184° C.; $[\alpha]_D^{25}$+τ° (c=0.05, water)].

EXAMPLE 32

One hundred and forty two mg of d-7α-[(2-deoxy-3,4-di-0-acetyl-β-D-erythro-pentopyranosyl)oxy]-9α-amino-9β-acetyl-7,8,9,10-tetrahydro-6,11-dihydroxy-5,12-naphthacenedione prepared in the same manner as in Example 11 was dissolved in 20 ml of dry methanol and 10 ml of dry dichloromethane. To this solution was added 157 mg of sodium cyanoborohydride at room temperature. Reaction was effected for 1.5 hour and thereafter the reaction mixture was poured into a cooled 5% aqueous sodium bicarbonate solution and extracted with dichloromethane. The organic layer was washed with water, dried over sodium sulfate and concentrated under reduced pressure to obtain 120 mg of a residue. This residue was purified by a silica gel column chromatography (eluant: 5% methanol/dichloromethane) to obtain d-7α-[(2-deoxy-3,4-di-0-acetyl-β-D-erythro-pentapyranosyl)oxy]-9α-amino-9β-(1-hydroxyethyl)-7,8,9,10-tetrahydro-6,11-dihydroxy-5,12-naphthacenedione in reddish brown crystal [m.p. 119°–121° C.; MS: [M]+ 569].

EXAMPLE 33

200 mg of d-7α-[(2,3,6-trideoxy-3-trifluoroacetamide-α-L-lyxo-hexopyranosyl)oxy]-9α-amino-9β-acetyl-7,8,9,10-tetrahydro-6,11-dihydroxy-5,12-naphthacenedione (m.p. 143°–145° C.; $[\alpha]_D^{25}$+184° (c=0.12, chloroform)] was dissolved in 4 ml of dimethylformamide. Then, to this solution were added 1.5 ml of dihydropyran and 110 mg of anhydrous p-toluenesulfonic acid and the mixture was stirred at room temperature for 1 hour. The reaction mixture was treated in the same manner as in Example 10 to obtain 230 mg of 7α-[(2,3,6-trideoxy-4-0-tetrahydropyranyl-3-trifluoro-acetamide-α-L-lyxo-hexopyranosyl)oxy]-9α-amino-9β-acetyl-7,8,9,10-tetrahydro-6,11-dihydroxy-5,12-naphthacenedione as a mixture of two diastereomers.

EXAMPLE 34

In 15 mL of MeOH was dissolved 200 mg of 7α-[(2,3,6-trideoxy-4-0-tetrahydropyranyl-3-trifluoroacetamide-α-L-lyxo-hexopyranosyl)oxy]-9α-amino-9β-acetyl-7,8,9,10-tetrahydro-6,11-dihydroxy-5,12-naphthacenedione. To this solution was added 7 ml of 10% aqueous potassium carbonate solution and this was stirred at 0°–5° C. overnight. The reaction mixture was neutralized with 3% aqueous hydrochloric acid solution, followed by adding a saturated aqueous sodium bicarbonate solution and extracting with chloroform. The chloroform layer was washed with water and then dried with sodium sulfate and chloroform was removed by distillation under reduced pressure to obtain a residue. This residue was purified by a silica gel column chromatography (eluant: 5% methanol/chloroform containing 0.5% aqueous ammonia) to obtain 7α-[(2,3,6-trideoxy-4-0-tetrahydropyranyl-3-amino-β-L-lyxo-hexapyranosyl)oxy]-9α-amino-9β-acetyl-7,8,9,10-tetrahydro-6,11-dihydroxy-5,12-naphthacenedione which comprised two diastereomers (abbreviated as 4′-THP A, B).

4′-THP-A: Rf 0.34 (silica gel, 7% methanol/chloroform containing 7% aqueous ammonia); m.p. 157°–164° C.; $[\alpha]_D^{31}$+143.8° (c=0.03, chloroform).

4'-THP-B: Rf 0.24 (silica gel, 7% methanol/chloroform containing 0.7% aqueous ammonia); m.p. 141°–147° C.; $[\alpha]_D^{31}+112.5°$ (c=0.03, chloroform).

EXAMPLE 35

In 3 ml of dimethylformamide was dissolved 140 mg of 7α-[(2,3,6-trideoxy-3-amino-α-L-lyxo-hexopyranosyl)oxy]-9α-amino-9β-acetyl-7,8,9,10-tetrahydro-6,11-dihydroxy-5,12-naphthacenedione (dihydrochloride, m.p. 176°–180° C.; $[\alpha]_D^{25}+149°$ (c=0.11, water)]. Then, to the solution were added 2.0 g of bis(2-iodoethyl) ether and 72 mg of triethylamine and this was stirred at room temperature overnight. The reaction mixture was poured into a saturated aqueous sodium bicarbonate solution and extracted with chloroform. Thereafter, the chloroform layer was washed with water, dried over sodium sulfate and the solvent was removed by distillation under reduced pressure to obtain a residue. This residue was purified by a silica gel column chromatography (eluant: 10% methanol/chloroform containing 0.5% aqueous ammonia) and then converted to hydrochloride with hydrochloric acid/ether to obtain 98 mg of d-7α-[(2,3,6-trideoxy-3-morpholino-α-L-lyxo-hexopyranosyl)oxy]-9α-amino-9β-acetyl-7,8,9,10-tetrahydro-6,11-dihydroxy-5,12-naphthacenedione di-hydrochloride [m.p. 178°–179° C.; $[\alpha]_D^{20}+156°$ (c=0.10, methanol)].

EXAMPLE 36

The 7 ml of dimethylformamide was dissolved 0.30 g of 1-9α-amino-9β-acetyl-7,8,9,10-tetrahydro-6,7α,11-trihydroxy-5,12-naphthacenedione hydrochloride $[[\alpha]_D^{20}-89°$ (c=0.1, DMF)]. Thereafter, to the solution were added 3 ml of 4,5-dihydrofuran and 10 mg of anhydrous p-toluenesulfonic acid and this was stirred at room temperature for 2 hours. The reaction mixture was added to a saturated aqueous sodium bicarbonate solution and extracted three times with chloroform. The chloroform layer was washed three times with a saturated aqueous sodium chloride solution, then dried over sodium sulfate and concentrated under reduced pressure. Thus obtained residue was purified by a silica gel column chromatography (eluant: 5% methanol/chloroform) to obtain 42 mg of 7-0-tetrahydrofuranyl-9α-amino-9β-acetyl-7,8,9,10-tetrahydro-6,7α,11-trihydroxy-5,12-naphthacenedione [m.p. 92°–100° C.; $[\alpha]_D^{30}+148°$ (c=0.07, chloroform)].

EXAMPLE 37

Reaction, after-treatments and purification were carried out in the same manner as in Example 5 using 116 mg of d-9α-amino-9β-acetyl-7,8,9,10-tetrahydro-6,7α,11-trihydroxy-5,12-naphthacenedione and 310 mg of 2,3,6-trideoxy-3-trifluoroacetamide-4-0-trifluoroacetyl-L-arabinohexopyranosyl chloride. There was obtained 46 mg of d-7α-[(2,3,6-trideoxy-3-trifluoroacetamide-α-L-arabino-hexopyranosyl)oxy]-9α-amino-9β-acetyl-7,8,9,10-tetrahydro-6,11-dihydroxy-5,12-naphthacenedione [m.p. 151°–154° C.; $[\alpha]_D^{31}+203°$ (c=0.11, chloroform)].

EXAMPLE 38

Reaction, the subsequent after-treatments and purification are carried out in the same manner as in Example 5 using 9α-amino-9β-acetyl-7,8,9,10-tetrahydro-6,7α,11-trihydroxy-5,12-naphthacenedione and 2,3,4,6-tetradeoxy-3-trifluoroacetamide-4-0-trifluoroacetyl-L-threo-hexopyranosyl chloride. There is obtained 7α-[(2,3,4,6-tetradeoxy-3-trifluoroacetamide-α-L-threo-hexopyranosyl)oxy]-9α-amino-9β-acetyl-7,8,9,10-tetrahydro-6,11-dihydroxy-5,12-naphthacenedione.

EXAMPLE 39

Hydrolysis of d-7α-[(2,3,6-trideoxy-3-trifluoroacetamide-α-L-arabino-hexopyranosyl)oxy]-9α-amino-9β-acetyl-7,8,9,10-tetrahydro-6,11-dihydroxy-5,12-naphthacenedione is made in the same manner as in Example 6 to obtain 7α-[(2,3,6-trideoxy-3-amino-α-L-arabino-hexopyranosyl)oxy]-9α-amino-9β-acetyl-7,8,9,10-tetrahydro-6,11-dihydroxy-5,12-naphthacenedione.

EXAMPLE 40

Reduction of 7α-[(2,3,6-trideoxy-3-amino-α-L-arabino-hexopyranosyl)oxy]-9α-amino-9β-acetyl-7,8,9,10-tetrahydro-6,11-dihydroxy-5,12-naphthacenedione is made in the same manner as in Example 28 to obtain 7α-[(2,3,6-trideoxy-3-amino-α-L-arabino-hexopyranosyl)oxy]-9α-amino-9β-(1-hydroxyethyl)-7,8,9,10-tetrahydro-6,11-dihydroxy-5,12-naphthacenedione.

EXAMPLE 41

Hydrolysis of 7α-[(2,3,4,6-tetradeoxy-3-trifluoroacetamide-α-L-threo-hexopyranosyl)oxy]-9α-amino-9β-acetyl-7,8,9,10-tetrahydro-6,11-dihydroxy-5,12-naphthacenedione is effected in the same manner as in Example 6 to obtain 7α-[(2,3,4,6-tetradeoxy-3-amino-α-L-threo-hexopyranosyl)oxy]-9α-amino-9β-acetyl-7,8,9,10-tetrahydro-6,11-dihydroxy-5,12-naphthacenedione.

EXAMPLE 42

Reduction of 7α-[(2,3,4,6-tetradeoxy-3-amino-α-L-threo-hexopyranosyl)oxy]-9α-amino-9β-acetyl-7,8,9,10-tetrahydro-6,11-dihydroxy-5,12-naphthacenedione is effected in the same manner as in Example 28 to obtain 7α-[(2,3,4,6-tetradeoxy-3-amino-α-L-threo-hexopyranosyl)oxy]-9α-amino-9β-(1-hydroxyethyl)-7,8,9,10-tetrahydro-6,11-dihydroxy-5,12-naphthacenedione.

EXAMPLE 43

Reaction is carried out in the same manner as in Example 35 using 7α-[(2,3,4,6-tetradeoxy-3-amino-α-L-threohexopyranoxyl)oxy]-9α-amino-9β-acetyl-7,8,9,10-tetrahydro-6,11-dihydroxy-5,12-naphthacenedione and bis(2-iodoethyl)ether to obtain 7α-[(2,3,4,6-tetradeoxy-3-morpholino-α-L-threohexopyranosyl)oxy]-9α-amino-9β-acetyl-7,8,9,10-tetrahydro-6,11-dihydroxy-5,12-naphthacenedione.

EXAMPLE 44

Reduction of 7α-[(2,3,4,6-tetradeoxy-3-morpholino-α-L-threo-hexopyranosyl)oxy]-9α-amino-9β-acetyl-7,8,9,10-tetrahydro-6,11-dihydroxy-5,12-naphthacenedione is carried out in the same manner as in Example 28 to obtain 7α-[(2,3,4,6-tetradeoxy-3-morpholino-α-L-threo-hexopyranosyl) oxy]-9α-amino-9β-(1-hydroxyethyl)-7,8,9,10-tetrahydro-6,11-dihydroxy-5,12-naphthacenedione.

EXAMPLE 45

Hydrolysis of d-7α-[(2,3,6-trideoxy-4-0-acetyl-α-L-erythro-hexopyranosyl)oxy]-9α-amino-9β-acetyl-7,8,9,10-tetrahydro-6,11-dihydroxy-5,12-naphthacenedione obtained in the same manner as in Example 16 is effected in the same manner as in Example 2 to obtain 7α-[(2,3,6-trideoxy-α-L-erythro-hexopyranosyl)oxy]-9α-amino-9β-acetyl-7,8,9,10-tetrahydro-6,11-dihydroxy-5,12-naphthacenedione.

EXAMPLE 46

Reaction of 7α-[(2,3,6-trideoxy-α-L-erythrohexopyranosyl)oxy]-9α-amino-9β-acetyl-7,8,9,10-tetrahydro-6,11-dihydroxy-5,12-naphthacenedione with dihydropyran in the same manner as in Example 33 gives 7α-[(2,3,6-trideoxy-3-0-tetrahydropyranyl-α-L-erythro-hexopyranosyl)oxy]-9α-amino-9β-acetyl-7,8,9,10-tetrahydro-6,11-dihydroxy-5,12naphthacenedione as a mixture of two diastereomers.

EXAMPLE 47

Example 19 is repeated using d-1-methoxy-9α-amino-9β-acetyl-6,7α, 11-trihydroxy-7,8,9,10-tetrahydro-5,12-naphthacenedione $[α]_D^{20}+123°$ (c=0.1, chloroform), to obtain d-7α-[(2-deoxy-3,4-di-0-acetyl-β-D-erythro-pentapyranosyl)oxy]- 1-methoxy-9α-amino-9β-acetyl-6,11-dihydroxy-7,8,9,10-tetrahydro-5,12-naphthacenedione in reddish orange crystal.

EXAMPLE 48

Example 19 is repeated using d-4-methoxy-9α-amino-9β-acetyl-6,7β, 11-trihydroxy-7,8,9,10-tetrahydroxy-5,12-naphthacenedione $[[α]_D^{20}+113°$ (c=0.1, chloroform)] and 2,6-dideoxy-3,4-di-0-acetyl-L-lyxo-hexopyranosyl chloride, to obtain d-7α-[(2,6-dideoxy-3,4-di-0-acetyl-L-lyxo-hexopyranosyl)oxy]-4-methoxy-9α-amino-9β-acetyl-6,11-dihydroxy-7,8,9,10-tetrahydro-5,12-naphthacenedione in reddish orange crystal.

EXAMPLE 49

Example 19 is repeated using d-1-methoxy-9α-amino-9β-acetyl-6,7β,11-trihydroxy-7,8,9,10-tetrahydro-5,12-naphthacenedione $[[α]_D^{20}+123°$, (c=0.1, chloroform) and 2,6-dideoxy-3,4-di-0-acetyl-L-lyxo-hexopyranosyl chloride to obtain d-7α-[(2,6-dideoxy-3,4-di-0-acetyl-L-lyxo-hexopyranosyl)oxy]-methoxy-9α-amino-9β-acetyl-6,11-dihydroxy-7,8,9,10-tetrahydro-5,12-naphthacenedione.

EXAMPLE 50

Example 22 is repeated using d-1-methoxy-9α-amino-9β-acetyl-6,7β,11-trihydroxy-7,8,9,10-tetrahydro-5,12-naphthacenedione $[[α]_D^{20}+123°$ (c=0.1, chloroform)] and 3-trifluoroacetamide-2,3,4,6-tetradeoxy-L-threo-hexopyranosyl chloride to obtain d-7α-[(3-trifluoroacetamide-2,3,4,6-tetradeoxy-α-L-threo-hexopyranosyl)oxy]-1-methoxy-9α-amino-9β-acetyl-6,11-dihydroxy-7,8,9,10-tetrahydro-5,12-naphthacenedione.

EXAMPLE 51

Example 23 is repeated using d-7α-[(3-trifluoroacetamide-2,3,4,6-tetradeoxy-α-L-threo-hexopyranosyl)oxy]-1-methoxy-9α-amino-9β-acetyl-6,11-dihydroxy-7,8,9,10-tetrahydroxy- 5,12-naphthacenedione obtained in Example 50 to obtain d-7α-[(3-amino-2,3,4,6-tetradeoxy-α-L-threohexopyranosyl)oxy]-1-methoxy-9α-amino-9β-acetyl-6,11-dihydro-7,8,9,10-tetrahydro-5,12-naphthacenedione in reddish brown crystal.

EXAMPLE 52

Example 22 is repeated using d-1-methoxy-9α-amino-9β-acetyl-7,8,9,10-tetrahydro-6,7β,11-trihydroxy-5,12-naphthacenedione and 2,3,6-trideoxy-3-trifluoroacetamide-4-0-trifluoroacetyl-L-arabino-hexopyranosyl chloride to obtain d-7α-[(2,3,6-trideoxy-3-trifluoroacetamide-α-L-arabino-hexopyranosyl)oxy]-1-methoxy-9α-amino-9β-acetyl-7,8,9,10-tetrahydro-6,11-dihydroxy-5,12-naphthacenedione.

EXAMPLE 53

Example 23 is repeated using d-7α-[(2,3,6-trideoxy-3-trifluoroacetamide-L-arabino-hexopyranosyl)oxy]-1-methoxy-9α-amino-9β-acetyl-7,8,9,10-tetrahydro-6,11-dihydroxy-5,12-naphthacenedione obtained in Example 52 to obtain d-7α-[(2,3,6-trideoxy-3-amino-α-L-arabino-hexopyranosyl)oxy]-1-methoxy-9α-amino-9β-acetyl-7,8,9,10-tetrahydro-6,11-dihydroxy-5,12-naphthacenedione.

EXAMPLE 54

Example 35 is repeated using d-7α-[(3-amino-2,3,4,6-tetradeoxy-α-L-threo-hexopyranosyl)oxy]-1-methoxy-9α-amino9β-acetyl-6,11-dihydroxy-7,8,9,10-tetrahydro 5,12-naphthacenedione obtained in Example 51 to obtain 7α-[(3-morpholino-2,3,4,6-tetradeoxy-α-L-threo-hexopyranoxyl)oxy]-1-methoxy-9α-amino-9β-acetyl-6,11-dihydro-7,8,9,10-tetrahydro-5,12-naphthacenedione.

EXAMPLE 55

Example 34 is repeated using d-7α-[(2,3,6-trideoxy-3-amino-α-L-arabino-hexopyranosyl)oxy]-1-methoxy-9α-amino-9β-acetyl-7,8,9,10-tetrahydro-6,11-dihydroxy-5,12-naphthacenedione obtained in Example 53 to obtain d-7α-[(2,3,6-trideoxy-3-amino-4-0-tetrahydropyranyl-α-L-arabinohexopyranosyl)oxy]-1-methoxy-9α-amino-9β-acetyl-5,12naphthacenedione as a mixture of two diastereomers.

EXAMPLE 56

Example 34 is repeated using d-7α-[(2,3,6-trideoxy-3-tri-fluoroacetamide-α-L-lyxo-hexopyranosyl)oxy]-4-methoxy-9α-amino-9β-acetyl-6,11-dihydroxy-7,8,9,10-tetrahydro-5,12naphthacenedione obtained in Example 20 to obtain d-7α-[(2,3,6-trideoxy-4-tetrahydropyranyl-3-trifluoroacetamide-α-L-lyxo-hexopyranosyl)oxy]-4-methoxy-9α-amino-9β-acetyl-6,11-dihydroxy-7,8,9,10-tetrahydro-5,12-naphthacenedione as a mixture of two diastereomers.

EXAMPLE 57

Reduction of 7α-0-tetrahydropyranyl-9α-amino-9β-acetyl-4-methoxy-7,8,9,10-tetrahydro-6,11-dihydroxy-5,12-naphthacenedione (7-THP-1) obtained in Example 26 is carried out in the same manner as in Example 27 to obtain 7α-0-tetrahydropyranyl-9α-amino-9β-(1-hydroxyethyl)-4-methoxy-7,8,9,10-tetrahydro-6,11-dihydroxy-5,12-naphthacenedione.

EXAMPLE 58

Reduction of 7α-[(2,3,6-trideoxy-3-amino-α-L-lyxohexopyranosyl)oxy]-9α-amino-9β-acetyl-1-methoxy-7,8,9,10-tetrahydro-6,11-dihydroxy-5,12-naphthacenedione obtained in Exmaple 23 is conducted in the same manner as in Example 27 to obtain 7α-[(2,3,6-trideoxy-3-amino-α-L-lyxo-hexopyranosyl) oxy]-9α-amino-9β-(1-hydroxyethyl)-1-methoxy-7,8,9,10-tetrahydro-6,11-dihydroxy-5,12-naphthacenedione.

EXAMPLE 59

Reduction of d-7α-[(2-deoxy-3,4-di-0-acetyl-β-D-erythropentapyranosyl)oxy]- 4-methoxy-9α-amino-9β-acetyl-6,11-dihydroxy-7,8,9,10-tetrahydro-5,12-naphthacenedione obtained in Example 19 is made in the same manner as in Example 27 to obtain 7α-[(2-deoxy-3,4-di-0-acetyl-α-Derythropentapyranosyl)oxy]-4-methoxy-9α-amino-9β-(1-hydroxyethyl)-6,11-dihydroxy-7,8,9,10-tetrahydro-5,12-naphthacenedione.

EXAMPLE 60

Example 27 is repeated using d-7α-[(2,3,6-trideoxy-3-amino-α-L-lyxo-hexopyranosyl)oxy]-9α-amino-9β-acetyl-4,6,11-trihydroxy-7,8,9,10-tetrahydro-5,12-naphthacenedione obtained in Example 25 to obtain 7α-[(2,3,6-trideoxy-3-amino-α-L-lyxo-hexopyranosyl)oxy]-9α-amino-9β-(1-hydroxyethyl)-4,6,11-trihydroxy-7,8,9,10-tetrahydro-5,12-naphthacenedione.

EXAMPLE 61

Example 35 is repeated using 7α-[(2,3,6-trideoxy-3-amino-α-L-lyxo-hexopyranosyl)oxy]-9α-amino-9β-(1-hydroxyethyl)-4,6,11-trihydroxy-7,8,9,10-tetrahydro-5,12-naphthacenedione obtained in Example 60 to obtain 7α-[(2,3,6-trideoxy-3-morpholino-α-L-lyxo-hexopyranosyl)oxy]-9α-amino-9β-(1-hydroxyethyl)-4,6,11-trihydroxy-7,8,9,10-tetrahydro-5,12-naphthacenedione.

EXAMPLE 62

To a solution of 27 mg of d-7α-[(2,3,6-trideoxy-3-morpholino-α-L-lyxo-hexopyranosyl)oxy]-9α-amino-9β-acetyl-7,8,9,10-tetrahydro-6,11-dihydroxy-5,12-naphthacenedione dihydrochloride obtained in Example 35 and 1 ml of dimethylformamide, was added 0.5 ml of dihydropyran and 6 mg of anhydrous p-toluenesulfonic acid. After stirring at room temperature overnight, the mixture was poured into a saturated sodium bicarbonate solution and then extracted twice with dichloromethane.

The combined organic phase was washed three times with a saturated sodium chloride solution, dried over sodium sulfate and then evaporated in vacuo to give a residue. This residue was purified by a preparative layer chromatography (silica gel, 5% methanol/chloroform containing 0.5% aqueous ammonia) to provide 30 mg of d-7α-[(2,3,6-trideoxy-3-morpholino-4-0-tetrahydropyranyl-α-L-lyxo-hexopyranosyl)oxy]-9α-amino-9β-acetyl-7,8,9,10-tetrahydro-6,11-dihydroxy-5,12-naphthacenedione [m.p. 72°–77° C., $[\alpha]_D^{27}+3.9°$ (c=0.1, chloroform)] as a mixture of two diastereomers.

REFERENCE EXAMPLES (1) A mixture of 6.75 g of 1-2-acetyl-2-acetamido-1,2,3,4-tetrahydro-5,8-dimethoxynaphthalene $[[\alpha]_D^{20}-128°$ (c=1, CHCl$_3$)], 9.97 g of 3-methoxyphthalic anhydride, 96.6 g of aluminum chloride and 19.3 g of sodium chloride was thoroughly ground. This mixture was introduced at a time into an eggplant type flask heated previously to 180° C. and kept at this temperature. After the mixture was molten, reaction was effected for 7 minutes. The reaction mixture was rapidly cooled to room temperature and subsequently added to 1000 ml of a saturated oxalic acid solution cooled with ice water. This was stirred at room temperature for 30 minutes and then precipitated crystal was collected by filtration to obtain a mixture of position isomers of 1-9-acetamino-9-acetyl-6,11-dihydroxy-7,8,9,10-tetrahydro-5,12-naphtacenedione which had a hydroxyl group at 1-position or 4-position [m.p. 287°–290° C.; IR(Nujol)cm$^{-1}$ 3340, 1695, 1660, 1595, 1520].

(2) Ten g of a mixture of 1-hydroxy and 4-hydroxy isomers of 1-9-acetamino-9-acetyl-6,11-dihydroxy-7,8,9,10-tetrahydro-5,12-naphthacenedione was dissolved in 2000 ml of dry acetone. To the solution were added 20.37 g of anhydrous potassium carbonate and 13.98 g of dimethylsulfuric acid. The mixture was refluxed and stirred for 22 hours. Inorganic materials were removed by filtration and filtrate was concentrated under reduced pressure. The resultant residue was dissolved in ethyl acetate and washed with 1N hydrochloric acid and water. Then, the solution was dried over sodium sulfate thereafter concentrated under reduced pressure. The resultant residue was purified by a silica gel column chromatography (ethyl acetate) to obtain a mixture of 1-methoxy and 4-methoxy isomers of 1-9-acetamino-9-acetyl-6,11-dimethoxy-7,8,9,10-tetrahydro-5,12-naphthacenedione [m.p. 151°–154° C.; IR(Nujol)cm$^{-1}$ 3600, 3350, 1710, 1680, 1590, 1530].

(3) Four point six g of a mixture of 1-methoxy and 4-methoxy isomers of l-9-acetamino-9-acetyl-6,11-dimethoxy-7,8,9,10-tetrahydro-5,12-naphthacenedione was dissolved in 918 ml of dry dichloromethane and to the solution was added 257 ml of 1% solution of boron trichloride in dichloromethane while cooling with dry ice-acetone. Reaction was carried out at this temperature for 10 minutes and thereafter the reaction mixture was poured into 300 ml of ice water. This was neutralized with a saturated aqueous sodium bicarbonate solution and then organic layer was separated, washed with water, then dried over sodium sulfate and concentrated under reduced pressure to obtain a mixture of 1-methoxy and 4-methoxy isomers of l-9-acetamino-9-acetyl-6,11-dihydroxy-7,8,9,10-tetrahydro-5,12-naphthacenedione. [m.p.>300° C. IR(Nujol)cm$^{-1}$ 3450, 3345, 1720, 1660, 1615, 1580, 1535].

(4) To 1.5 g of a mixture of 1-methoxy and 4-methoxy isomers of 1-9-acetamino-9-acetyl-6,11-dihydroxy-7,8,9,10-tetrahydro-5,12-naphthacenedione were added 670 ml of dry benzene, 44.1 ml of ethylene glycol and 0.67 g of p-toluenesulfonic acid and reaction was effected for 5 hours under refluxing with removal of co-boiling water. The reaction mixture was cooled, then washed with water, dried with sodium sulfate and concentrated under reduced pressure. The resultant residue was purified by a silica gel column chromatography (50% n-hexane/acetone) to obtain a mixture of 1-methoxy and 4-methoxy isomers of l-9-acetamino-9-(1-ethylenedioxy)ethyl-6,11-dihydroxy-7,8,9,10-tetrahydro-5,12-naphthacenedione [m.p. 163°–165° C.; IR(Nujol)cm$^{-1}$ 3550, 3300, 1670, 1610, 1580].

(5) One point four five g of a mixture of 1-methoxy and 4-methoxy isomers of l-9-acetamino-9-(1-ethylenedioxy) ethyl-6,11-dihydroxy-7,8,9,10-tetrahydro-5,12-naphthacenedione was dissolved in 88.4 ml of dry chloroform and 177 ml of dry carbon tetrachloride under refluxing. Then, to the solution was added 1.14 g of N-bromosuccinimide and the mixture was refluxed for 45 minutes while irradiating with 500 W visible light lamp. The reaction mixture was dissolved in chloroform while cooling with ice water and the solution was washed with a saturated aqueous sodium bicarbonate solution and water in order. The organic layer was dried over sodium sulfate and concentrated under reduced pressure to obtain a residue. This residue was purified by a silica gel column chromatography (3% methanol/dichloromethane) to separate 1-methoxy isomer and 4-methoxy isomer of d-9β-(1-ethylenedioxy)ethyl-6,11-dihydroxy-7,8,9,10-tetrahydro-7α,9α-(1-oxa-3-aza-2-methyl-2-propeno)-5,12-naphthacenedione. 4-methoxy isomer: NMR(CDCl$_3$)δ: 1.37(3H), 1.75(3H), 1.8–2.15(2H), 2.75–3.0(2H), 3.94(7H), 5.6–5.75(1H), 7.25(1H), 7.65(1H), 7.9(1H), 13.3–13.76(2H); m.p. 230–235° C.; IR(Nujol)cm$^{-1}$ 1660, 1620, 1580; MS: [M]$^+$ 465 1-methoxy isomer: m.p. 225°–228° C.; MS: [M]$^+$ 465.

(6)(i) To 197 mg of d-4-methoxy-9β-(1-ethylenedioxy)ethyl-6,11-dihydroxy-7,8,9,10-tetrahydro-7α,9α-(1-oxa-3-aza-2-methyl-2-propeno)-5,12-naphthacenedione were added 39.4 ml of dioxane, 39.4 ml of water and 9.85 ml of concentrated hydrochloric acid and the mixture was refluxed for 13 hours. The solvent was removed by distillation under reduced pressure to obtain a residue. This residue was dissolved in 70 ml of methanol, followed by adding 30 mg of active carbon and stirring. Insoluble materials were removed by filtration and the filtrate was concentrated under reduced pressure to obtain a residue. This residue was crystallized with isopropyl alcohol to obtain d-4-methoxy-9α-amino-9β-acetyl-6,7α,11-trihydroxy-7,8,9,10-tetrahydro-5,12-naphthacenedione hydrochloride (m.p. 212°–219° C.).

(6)(ii) One hundred and forty three mg of d-4-methoxy-9α-amino-9β-acetyl-6,7α,11-trihydroxy-7,8,9,10-tetrahydro-5,12-naphthacenedione hydrochloride obtained in (i) was dissolved in 100 ml of a cooled 3% aqueous hydrochloric acid solution and the solution was washed with 50 ml of ethyl acetate. The aqueous hydrochloric acid layer was neutralized with a saturated aqueous sodium bicarbonate solution, then extracted with chloroform (100 ml×2), washed with 50 ml of a saturated aqueous sodium chloride solution and then dried. After concentration under reduced pressure, the resultant residue was washed with ether to obtain the compound in the free form [m.p. 162°–163° C.; IR(Nujol)cm$^{-1}$ 3360, 1710, 1620, 1585; $[\alpha]_D^{20}$+113° (c=0.1, CHCl$_3$; MS: [M+1]$^+$ 398].

(7)(i) The same reaction as in (6) above was repeated using 315 mg of d-1-methoxy-9β-(1-ethylenedioxy)ethyl-6,11-dihydroxy-7,8,9,10-tetrahydro-7α,9α-(1-oxa-3-aza-2-methyl-2-propeno)-5,12-naphthacenedione, to obtain d-1-methoxy-b 9α-amino-9β-acetyl-6,7α,11-trihydroxy-7,8,9,10-tetrahydro-5,12-naphthacenedione hydrochloride (m.p. 233°–237° C.).

(7)(ii) The same reaction as in (6)(ii) above was repeated using 239 mg of d-1-methoxy-9α-amino-9β-acetyl-6,7α,11-trihydroxy-7,8,9,10-tetrahydro-5,12-naphthacenedione hydrochloride obtained in (7)(i), to obtain the compound in a free form [m.p. 178°–180° C.; IR(Nujol)cm$^{-1}$ 3350, 1705, 1620, 1585; $[\alpha]_D^{20}$+123° (c=0.1, CHCl$_3$); MS: [M+1]$^+$ 398].

(8) Three hundred mg of d-4-methoxy-9α-amino-9β-acetyl-6,7α,11-trihydroxy-7,8,9,10-tetrahydro-5,12-naphthacenedione obtained in (6) was dissolved in 30 ml of dry dichloromethane. Under refluxing, to the solution was added 907 mg of anhydrous aluminum chloride over a period of about 10 minutes. Reaction was effected at this temperature for 5 hours and the reaction mixture was poured into 160 ml of a saturated aqueous oxalic acid solution. This mixture was stirred at room temperature for 30 minutes and neutralyzed with a saturated aqueous sodium bicarbonate solution. The dichloromethane layer was washed with water, then dried over sodium sulfate and concentrated under reduced pressure. The resultant residue was washed with ether to obtain d-9α-amino-9β-acetyl-4,6,7α,11-tetrahydroxy-7,8,9,10-tetrahydro-5,12-naphthacenedione [m.p. 138°–140° C.; IR(Nujol)cm$^{-1}$ 3200–3400, 1700, 1580, 1570; MS: [M+1]$^+$ 384].

In the above Examples and Reference Examples the mass spectrometric analysis was in accordance with field desorption spectrum.

Pharmacological test

1. Test methods (1) Effect against P388 mouse leukemia cell (in vitro test)

P388 leukemia cells have been subcultured in abdominal cavity of DBA/2 mouse. Cells are collected from the cavity and are suspended in a Rosewell Park Memorial Institute medium 1640 containing 10% blood serum of young cow, 5 μM 2-hydroxyethyl disulfide, 100 μg/ml Streptomycin and 100 U/ml Penicillin. A suspension of 5×10$^4$ cells/ml containing a test compound is prepared and is cultured in a wet atmosphere containing 5% CO$_2$ at 37° C. for 48 hours.

Number of cells before and after culturing is counted by coulter counter. Proliferative ratio is defined as ratio of the increase in cells after proliferation for 48 hours to an increase in cells cultured in a suspension containing no test compound. Inhibition ratio (IR) is defined as follows:

1—(proliferative ratio).

In other words, $$\text{Inhibition ratio (\%)} = \left(1 - \frac{C^{treated} - C_o}{C^{non} - C_o}\right) \times 100$$

where $C^{treated}$: number of cells after culturing for 48 hours in the presence of a treated compound $C^{non}$: number of cells after culturing for 48 hours in the absence of a test compound $C_o$: number of cells when culturing is initiated.

(2) Effect against survival time of mouse transplanted with P388 mouse leukemia cells (in vivo test, intraperitoneal administration)

Tumor: P388 mouse leukemia.

Animals: CDF$_1$ (BALB/C×DBA/2) mouse ♂ 5 weeks breeding, one group: 6 mice.

Number of cells transplanted: 10$^6$/mouse, intraperitoneal administration.

Dosage: Test compound administered twice, i.e. the first and fifth days, intraperitoneally. Test compound hardly soluble or insoluble in water is applied in a solution or a suspension form by use of Tween 80.

Controls: Non-treated; separately and positive control where ADR* 4 mg/kg administered twice, i.e. the first and fifth days.
ADR: Adriamycin Evaluation: Increase life span (ILS) is calculated on the basis of median survival times (T) and (C) of treated groups and controls, repsctively:

$$ILS(\%) = \frac{T}{C} - 100$$

(3) Effect against survival times of mouse transplanted with P388 mouse leukemia cells (in vivo test; intravenous or per os administration)

Similar to (2), but a test compound administered once, i.e., only the first day, intravenously or orally.

2. Test Result

Table 1 shows results of tests (1) and (2) above. Tables 2 and 3 show results of test (3) above.

TABLE 1

| Compound (Example No. | | in vitro (γ/ml) IR (%) | | | | in vivo (mg/kg) ILS (%) | | | | | | | | |
|---|---|---|---|---|---|---|---|---|---|---|---|---|---|---|
| | | 10 | 1 | $10^{-1}$ | $10^{-2}$ | | 25 | 12.5 | 6.25 | 3.13 | 1.56 | 8 | 4 | 2 | 1 |
| 1 | | 82.7 | 84.1 | 32.4 | | | 152 | 86 | 42 | | | | | | |
| | ADR | 90.6 | 85.9 | 85.0 | | ADR | | | | | | | 133 | 105 | 58 |
| 2 | | 89.9 | 84.5 | 44.1 | | | | 135 | | | | | | | |
| | ADR | 90.6 | 85.9 | 85.0 | | ADR | | | | | | | 133 | 105 | 58 |
| 10-A | | 89.0 | 94.4 | 94.6 | | | 286 | 77 | 25 | | | | | | |
| | ADR | 92.1 | 90.4 | 81.1 | | ADR | | | | | | | 105 | 90 | 78 |
| 11 (hydrochloride) | | 100 | 97.9 | 1.9 | | | 280 | 123 | 37 | | | | | | |
| | ADR | 100 | 100 | 100 | | ADR | | | | | | 101 | 96 | 84 | 57 |
| 12 (hydrochloride) | | 85.0 | 83.8 | 27.5 | | | | | | | | | | | |
| | ADR | 98.1 | 91.1 | 91.8 | | | | | | | | | | | |
| 25 (dihydrochloride) | | 99.4 | 95.7 | 89.0 | | | | | | | | | | | |
| | ADR | 98.5 | 94.0 | 94.0 | | | | | | | | | | | |
| 29 | | 94.1 | 92.9 | 93.5 | 40.1 | | | 126 | 66 | | | | | | |
| | ADR | 93.6 | 91.2 | 93.5 | 69.2 | ADR | | | | | | | 105 | 90 | 78 |

TABLE 2

| | (iv administered) | | |
|---|---|---|---|
| Compound (Example No.) | Dose (mg/kg) | ILS (%) | Toxic Death |
| 12 (hydrochloride) | 10 | 32 | |
| | 20 | 60 | |
| | 40 | −43 | 6/6 |
| 11 (hydrochloride) | 10 | 35 | |
| | 20 | 67 | |
| | 40 | −45 | 6/6 |
| ADR | 3.75 | 21 | |
| | 7.5 | 47 | |
| | 15 | 83 | |

TABLE 3

| | (po administered) | | |
|---|---|---|---|
| Compound (Example No.) | Dose (mg/kg) | ILS (%) | Toxic Death |
| 12 hydrochloride | 17.5 | 31 | |
| | 35 | 50 | |
| | 70 | 86 | |
| 11 (hydrochloride) | 17.5 | 40 | |
| | 35 | 63 | |
| | 70 | −42 | 6/6 |
| ACM-A* | 10.7 | 11 | |
| | 21.5 | 25 | |
| | 43 | 37 | |

*ACM-A: Aclacinomycin-A

Toxicity test

1. Test method

One tenth ml each 10 kg of body weight of solutions of testing compounds or adriamycin, which are prepared with isotonic sodium chloride solution, are applied once to groups of BALB/C mice, i.e., ten mice a group, to see whether or not they die and change in body weight. Amounts applied are 50, 40, 32, 25 and 20 mg/kg for the testing compounds and 20, 16, 12.5, 10 and 8 mg/kg for adriamycin. The largest amount where no death of mice is seen is defined as maximum tolerated dose.

2. Result

| Compound (Example No.) | MTD* (mg/kg) |
|---|---|
| 11 (hydrochloride) | 40 |
| 12 (hydrochloride) | 32 |
| Adriamycin | 12.5 |

*MTD: Maximum tolerated dose

We claim:

1. 9-Aminonaphthacene derivative having the formula:

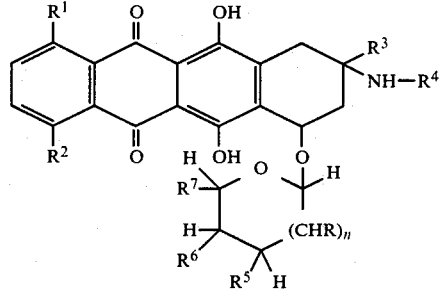

wherein $R^1$ and $R^2$ are both hydrogen atoms or either one of them is a hydrogen atom and the other is hydroxy group or methoxy group; $R^3$ is acetyl group or 1-hydroxyethyl group; $R^4$ is a hydrogen atom; $R^5$ is a hydrogen atom, hydroxy group, lower alkanoyloxy group or amino group; $R^6$ is a hydrogen atom, hydroxy group or lower alkanoyloxy group; $R^7$ is a hydrogen atom or methyl group; R is a hydrogen atom; and n is one.

2. A compound according to claim 1 wherein both $R^1$ and $R^2$ are hydrogen atoms.

3. A compound according to claim 1 wherein $R^1$ is methoxy group and $R^2$ is a hydrogen atom.

4. A compound according to claim 1 wherein $R^1$ is a hydrogen atom and $R^2$ is methoxy group.

5. A compound according to claim 1 wherein either $R^1$ or $R^2$ is a hydrogen atom and the other is hydroxy group.

6. A compound accroding to claim 1 wherein $R^3$ is acetyl group.

7. A compound according to claim 1 wherein $R^3$ is 1-hydroxyethyl group.

8. A compound according to claim 1 wherein $R^5$ is amino group, $R^7$ is methyl group.

9. A compound accroding to claim 1 wherein both $R^5$ and $R^6$ are hydroxy groups or acetoxy groups.

10. A compound according to claim 9 wherein $R^7$ is methyl group.

11. A compound according to claim 9 wherein $R^7$ is a hydrogen atom.

12. A compound according to claim 1 wherein $R^5$, $R^6$ and $R^7$ all are hydrogen atoms.

13. A compound according to claim 8 wherein $R^6$ is a hydrogen atom.

14. A compound according to claim 1 which is d-7α-[(2-deoxy-β-D-erythro-pentapyranosyl)oxy]-9α-amino-9β-acetyl-7,8,9,10-tetrahydro-6,11-dihydroxy-5,12-naphthacenedione.

15. A compound according to claim 1 which is d-7α-[(2-deoxy-3,4-di-0-acetyl-β-D-erythro-pentapyranosyl)oxy]-9α-amino-9β-acetyl-7,8,9,10-tetrahydro-6,11-dihydroxy-5,12-naphthacenedione.

16. A compound according to claim 1 which is d-7α-[(2-deoxy-β-D-erythro-pentapyranosyl)oxy]-9α-amino-9β-acetyl-7,8,9,10-tetrahyro-6,11-dihydroxy-5,12-naphthacenedione.

17. A compound according to claim 1 which is a d-7α-[(2-deoxy-3,4-di-O-acetyl-β-D-erythro pentapyranosyl)oxy]-9α-amino-9β-acetyl-7,8,9,10-tetrahydro-6,11-dihydroxy-5-12-napthacenedione.

18. A pharmaceutical composition useful against P 388 Mouse Leukemia cells which comprises an effective amount of a compound of claim 1 as an active ingredient and a pharmaceutically acceptable carrier or diluent.

19. A method of inhibiting the growth of P 388 mouse leukemia cells in a mouse comprising administering to a mouse having P 388 mouse leukemia cells an amount of a compound of claim 1 to inhibit the growth of the P 388 mouse leukemia cells sufficiently to increase the life span of the mouse.

* * * * *